United States Patent
Saville et al.

(10) Patent No.: US 12,234,445 B2
(45) Date of Patent: Feb. 25, 2025

(54) GLYCOGEN-NULL METHANOTROPHS AND USES THEREOF

(71) Applicant: Calysta, Inc., Menlo Park, CA (US)

(72) Inventors: Renee M. Saville, Mountain View, CA (US); Joshua A. Silverman, Los Altos Hills, CA (US); Vincent Tang, Menlo Park, CA (US); Eric G. Luning, Sunnyvale, CA (US); Paloma Rueda, Menlo Park, CA (US); Megan Hsi, Menlo Park, CA (US); Yelena Stegantseva, Menlo Park, CA (US)

(73) Assignee: Calysta, Inc., Menlo Park, CA (US)

( * ) Notice: Subject to any disclaimer, the term of this patent is extended or adjusted under 35 U.S.C. 154(b) by 757 days.

(21) Appl. No.: 17/293,832

(22) PCT Filed: Dec. 26, 2019

(86) PCT No.: PCT/US2019/068614
§ 371 (c)(1),
(2) Date: May 13, 2021

(87) PCT Pub. No.: WO2020/139974
PCT Pub. Date: Jul. 2, 2020

(65) Prior Publication Data
US 2022/0010268 A1   Jan. 13, 2022

Related U.S. Application Data

(60) Provisional application No. 62/785,668, filed on Dec. 27, 2018.

(51) Int. Cl.
| | | |
|---|---|---|
| *C12N 1/32* | (2006.01) | |
| *C12N 1/30* | (2006.01) | |
| *C12N 9/10* | (2006.01) | |
| *C12N 9/12* | (2006.01) | |
| *C12N 9/90* | (2006.01) | |
| *C12P 13/04* | (2006.01) | |
| *C12P 21/00* | (2006.01) | |

(52) U.S. Cl.
CPC ............. *C12N 1/32* (2013.01); *C12N 1/30* (2013.01); *C12N 9/1051* (2013.01); *C12N 9/1241* (2013.01); *C12N 9/90* (2013.01); *C12P 13/04* (2013.01); *C12P 21/00* (2013.01); *C12Y 204/01011* (2013.01); *C12Y 207/07027* (2013.01); *C12Y 504/02002* (2013.01); *C12N 2500/05* (2013.01); *C12N 2500/30* (2013.01)

(58) Field of Classification Search
CPC .......... C12N 1/32; C12N 1/30; C12N 9/1051; C12N 9/1241; C12N 9/90; C12N 2500/05; C12N 2500/30; C12P 13/04; C12P 21/00; C12Y 204/01011; C12Y 207/07027; C12Y 504/02002
See application file for complete search history.

(56) References Cited

U.S. PATENT DOCUMENTS

| 6,818,424 B2 | 11/2004 | DiCosimo et al. |
|---|---|---|
| 2002/0137190 A1 | 9/2002 | Koffas et al. |
| 2003/0003528 A1 | 1/2003 | Brzostowicz et al. |
| 2007/0059790 A1 | 3/2007 | Miller et al. |
| 2008/0026005 A1 | 1/2008 | Miguez et al. |

FOREIGN PATENT DOCUMENTS

| WO | 2014/205146 A1 | 12/2014 |
|---|---|---|
| WO | 2015/109257 A1 | 7/2015 |
| WO | 2015/175946 A1 | 11/2015 |
| WO | 2017/075440 A1 | 5/2017 |

OTHER PUBLICATIONS

Ward N. et al., "Genomic insights into methanotrophy: The complete genome sequence of Methylococcus capsulatus (Bath)", PLOS Biology, Oct. 2004, vol. 2, issue 10, e303 (DOI: 10.1371/journal.pbio.0020303.g001); pp. 1616-1628. (Year: 2004).*
Akhverdyan et al., "Application of the bacteriophage Mu-driven system for the integration/amplification of target genes in the chromosomes of engineered Gram-negative bacteria-mini review," *Appl Microbiol Biotechnol* 91:857-871 (2011).
Ali et al., "Duplication of the *mmoX* gene in *Methylosinus sporium*: cloning, sequencing and mutational analysis," *Microbiology* 152:2931-2942 (2006).
Benson et al., "Factors Altering Pyruvate Excretion in a Glycogen Storage Mutant of the Cyanobacterium, Synechococcus PCC7942," *Front. Microbiol.* 7(475), 11 pages, (Apr. 2016).
Bruss et al., "Enzymatic Microdetermination of Glycogen," *Analytical Biochemistry* 84:309-312 (1978).
Eshinimaev et al., "Physiological, Biochemical, and Cytological Characteristics of a Haloalkitolerant Methanotroph Grown on Methanol," *Microbiology* 71(5):512-518 (2002).
Fei et al., "Enhanced biological fix tion of methane for microbial lipid production by recombinant *Methylomicrobium buryatense*," *Biotechnol Biofuels* 11:129, 11 pages (2018).
Goh et al., "A functional glycogen biosynthesis pathway in *Lactobacillus acidophilus*: expression and analysis of the glg operon," *Molecular Microbiology* 89(6):1187-1200 (2013).
Linton et al., "The Occurrence and Identification of Intracellular Polyglucose Storage Granules in *Methylococcus* NCIB 11083 Grown in Chemostat Culture on Methane," *Arch Microbiol.* 117:41-48 (1978).
Puri et al., "Genetic Tools for the Industrially Promising Methanotroph *Methylomicrobium buryatense*," *Applied and Environmental Microbiology* 81(5):1775-1781 (Mar. 2015).
Smart et al., "Analytical platform for metabolome analysis of microbial cells using methyl chloroformate derivatization followed by gas chromatography-mass spectrometry," *Nature Protocols* 5(10):1709-1729 (2010).

(Continued)

Primary Examiner — Satyendra K Singh
(74) Attorney, Agent, or Firm — Seed IP Law Group LLP

(57) ABSTRACT

The present disclosure provides methanotrophic bacteria that are modified to produce less glycogen, and methods of using the modified methanotrophic bacteria to produce a desired product, such as protein(s) or metabolite(s).

33 Claims, 5 Drawing Sheets

Specification includes a Sequence Listing.

(56) References Cited

OTHER PUBLICATIONS

Stolyar et al., Role of multiple gene copies in particulate methane monooxygenase activity in the methane-oxidizing bacterium *Methylococcus capsulatus* Bath, *Microbiology* 145:1235-1244 (1999).
Toyama et al., "pqqA is not required for biosynthesis of pyrroloquinoline quinone in *Methylobacterium extorquens* AM1," *Microbiology* 144:183-191 (1998).
Van Dien et al., "Reconstruction of $C_3$ and $C_4$ metabolism in *Methylobacterium extorquens* AM1 using transposon mutagenesis," *Microbiology* 149:601-609 (2003).
Wilson et al., "Regulation of glycogen metabolism in yeast and bacteria," *FEMS Microbiol Ref.* 34(6):952-985 (Nov. 2010).

\* cited by examiner

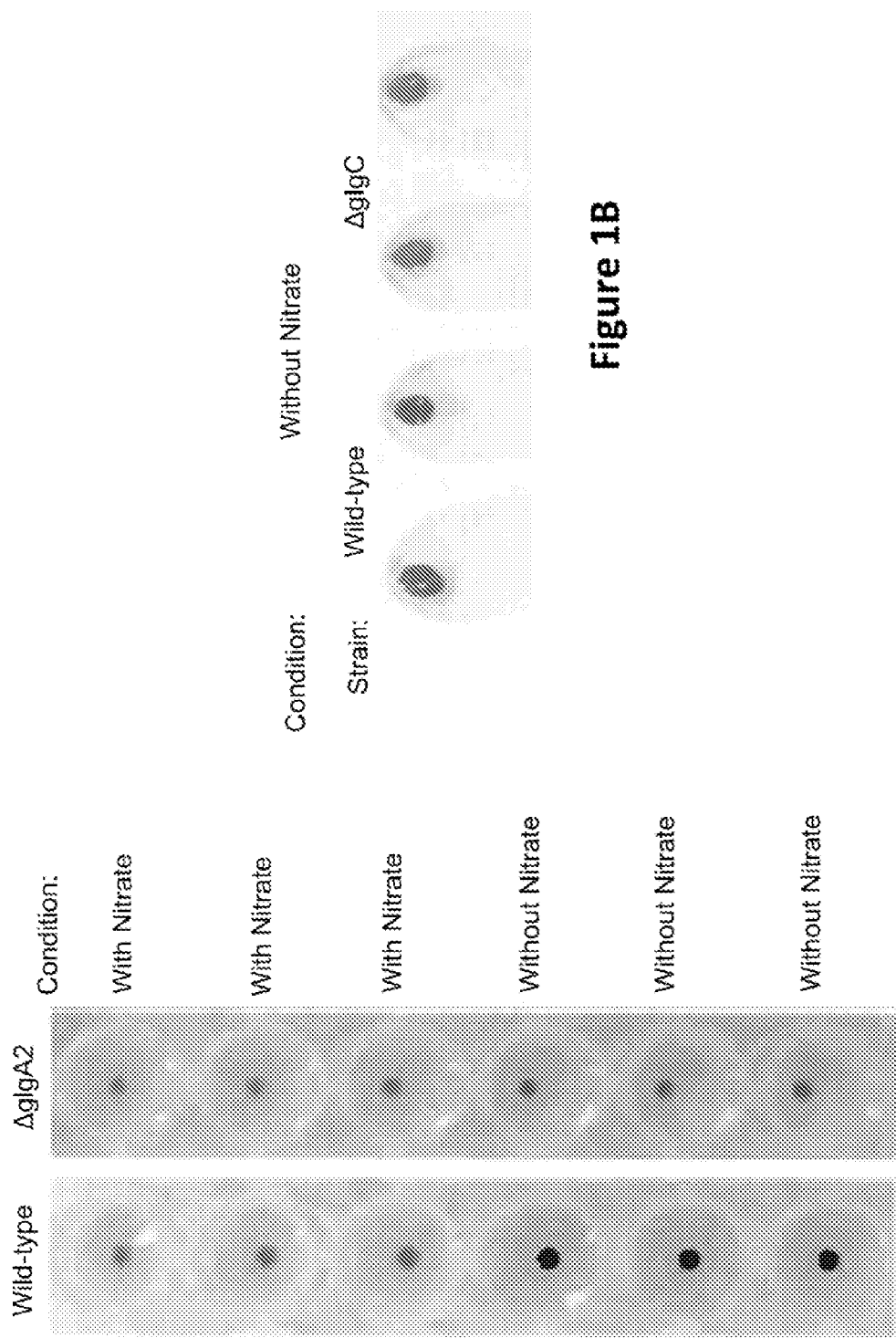

GLYCOGEN-NULL METHANOTROPHS AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200206_435USPC_SEQUENCE_LISTING. The text file is 28.1 KB, was created on May 13, 2021, and is being submitted electronically via EFS-Web.

BACKGROUND

Methanotrophic and methylotrophic bacteria utilize single-carbon compounds, such as methane or methanol, as a source of carbon and energy. These bacteria are a useful tool for producing biofuels, reducing methane release into the atmosphere, and reducing environmental contaminants such as certain chlorinated hydrocarbons. However, under starvation conditions temporarily present in the environment or during fermentation, methanotrophic and methylotrophic bacteria (like many microorganisms) accumulate carbon and energy reserves as a coping mechanism. The biosynthesis of glycogen and starch is a main strategy for such metabolic storage. Glycogen is a major intracellular reserve polymer that is made up of α-1,4-linked glucose subunits with α-1,6-linked glucose at the branching points. In bacteria, the average length of the glycogen chains ranges from about 8 to 12 glucose units, and the molecular size of glycogen has been estimated to be about $10^7$ to $10^8$ Daltons (see Wilson et al., *FEMS Microbiol. Rev.* 34:952, 2010). The enzymology of the glycogen biosynthetic and degradative processes is highly conserved in most bacterial species (Ballicora et al., *Microbiol. Mol. Biol. Rev.* 67:213, 2003).

For a fermentation process in which bacteria have been engineered to maximize the production of a product(s) of interest, it would be desirable to block or reduce the storage of carbon in the form of glycogen, which functions as a carbon sink that would make achieving high cell density and/or production of products of interest less efficient. There is a need in the art for alternative methods for maximizing carbon flux in the production of products of interest. The present disclosure meets such needs, and further provides other related advantages.

BRIEF DESCRIPTION OF THE DRAWINGS

FIGS. 1A and 1B show iodine assay results for: (FIG. 1A) wild-type *Methylococcus capsulatus* Bath versus *M. capsulatus* Bath having a glgA mutation (ΔglgA), when grown in the presence or absence of nitrate; and (FIG. 1B) wild-type *M. capsulatus* Bath versus *M. capsulatus* Bath having a glgC mutation (ΔglgC) grown in the absence of nitrate. The presence of glycogen is indicated by the dark brownish-black stains.

(FIG. 3A) Luvulinate levels in the ΔglgC strain (shown as "Glycogen knock out") and a wild-type control, as measured by GCMS, are shown. (FIG. 3B) Crude protein levels in the ΔglgC strain (shown as "Gly(-)") and a wild-type control ("Wt") are shown.

(FIG. 5A) Dry cell weight production rate (g/h) is shown as a function of increasing nitrogen limitation. (FIG. 5B) Nitrogen production rate (mg/h) is shown as a function of increasing nitrogen limitation.

BRIEF SUMMARY

Figure 2B:
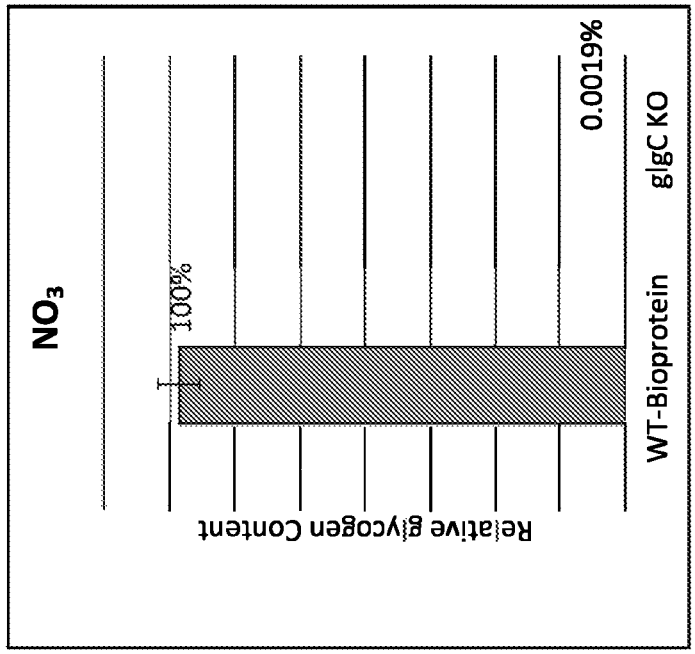
FIGS. 2A and 2B show relative glycogen production, as measured by an enzymatic assay, for wild-type *M. capsulatus* Bath versus the *M. capsulatus* Bath ΔglgC strain under nitrogen limited conditions (FIG. 2A) and nitrogen unlimited conditions (FIG. 2B).

The present disclosure provides $C_1$ metabolizing bacteria that are modified to produce less glycogen, and methods of using the modified $C_1$ metabolizing bacteria to produce a desired product, such as proteins or metabolites.

In one aspect, the present disclosure provides a modified *Methylococcus capsulatus*, comprising a chromosomal knock-out of an ADP-glucose pyrophosphorylase gene, a glgA2 isoform of a glycogen synthase gene, or both, wherein the modified *Methylococcus capsulatus* cultured under conditions comprising a non-limiting amount of a $C_1$ substrate produces: (i) at least about 30% less glycogen as compared to the parent *Methylococcus capsulatus* cultured under the same conditions; and/or (ii) at least about 5% more crude protein as compared to the parent *Methylococcus capsulatus* cultured under the same conditions.

In another aspect, the present disclosure provides a method of producing a desired product, the method comprising culturing a glycogen-null modified *Methylococcus capsulatus* under conditions comprising a non-limiting amount of a $C_1$ substrate and for a time sufficient to produce the desired product, wherein the quantity of the desired product is greater than a quantity of the desired product produced by the parental *Methylococcus capsulatus* cultured under the same conditions.

Other objectives, advantages and novel features of the disclosure will become more apparent from the following detailed description.

DETAILED DESCRIPTION

The instant disclosure provides non-naturally occurring $C_1$ metabolizing bacteria that produce a reduced amount or no glycogen, and related compositions and methods of making such methanotrophs that produce less glycogen. In certain embodiments, modified methanotrophic bacteria of this disclosure produce less glycogen when having one or more glycogen biosynthesis genes knocked-out, one or more glycogen catabolism genes expressed or upregulated, or a combination thereof. The glycogen-altered methanotrophic microorganisms may be used for the expression or production of a desired product (e.g., protein) where controlled cultivation on a $C_1$ substrate is desired. In some embodiments, modified $C_1$ metabolizing bacteria further include a modification to one or more other non-glycogen biosynthesis or catabolism genes, for the production of one or more desired products (e.g., amino acids, protein) using the modified bacteria.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include any subrange within the range, the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

The term "consisting essentially of" is not equivalent to "comprising" and refers to the specified materials or steps of a claim, or to those that do not materially affect the basic characteristics of the claimed subject matter. For example, a protein domain, region, or module (e.g., an enzymatic domain, binding domain, or the like) or a protein (which may have one or more domains or regions) "consists essentially of" a particular amino acid sequence when the amino acid sequence of a domain, region, or protein includes an addition, deletion, substitution, or any combination thereof that, in combination, contributes to at most 20% (e.g., at most 15%, 10%, 8%, 6%, 5%, 4%, 3%, 2% or 1%) of the length of a domain, region, or protein and do not substantially affect the activity (i.e., do not reduce the activity by more than 50%, such as no more than 40%, 30%, 25%, 20%, 15%, 10%, 5%, or 1%) of the domain(s), region(s), module(s), or protein (e.g., enzymatic activity). Any ranges provided herein include all the values and narrower ranges in the ranges.

As used herein, "nucleic acid molecule" or "polynucleotide" refers to a polymeric compound comprised of covalently linked subunits called nucleotides. Examples of polynucleotides include polyribonucleic acid (RNA), polydeoxyribonucleic acid (DNA), both of which may be single or double stranded. DNA includes cDNA, genomic DNA, synthetic DNA, semi-synthetic DNA, or the like. In certain embodiments, protein(s) may be encoded by a polynucleotide located on a single nucleic acid molecule (e.g., a plasmid or a bacterial chromosome) or may be encoded by a polynucleotide located on more than one nucleic acid molecule—that is, polynucleotides located on different nucleic acid molecules can comprise all the coding sequences for exogenous proteins (e.g., glycogen catabolism enzymes and/or biosynthesis enzymes).

The phrase "control element" or "expression control sequence" means a nucleic acid sequence that directs transcription, such as, for example, a promoter or an enhancer, of a nucleic acid molecule or polynucleotide (e.g., gene) to which it is operatively linked.

The term "operably linked" or "operatively linked" refers herein to a configuration in which a control sequence (e.g., promoter) is appropriately placed at a position relative to a polynucleotide (e.g., gene) such that the control sequence influences the expression of the polynucleotide, which control sequence, polynucleotide, or both may be native or heterologous to the methanotrophic bacterium, provided that at least one of the control sequence and the polynucleotide is heterologous to the methanotrophic bacterium.

As used herein, the term "$C_1$ substrate" or "$C_1$ compound" refers to an organic compound lacking carbon to carbon bonds. $C_1$ substrates include natural gas, unconventional natural gas, methane, methanol, formaldehyde, formic acid (formate), carbon monoxide, carbon dioxide, methylated amines (e.g., methylamine, dimethylamine, trimethylamine, etc.), methylated thiols, methyl halogens (e.g., bromomethane, chloromethane, iodomethane, dichloromethane, etc.), syngas, and cyanide. In certain embodiments, a $C_1$ substrate comprises methane.

As used herein, "methane" refers to the simplest alkane compound with the chemical formula $CH_4$. Methane is a colorless and odorless gas at room temperature and pressure. Sources of methane include natural sources, such as natural gas fields, "unconventional natural gas" sources (such as shale gas or coal bed methane, wherein content will vary depending on the source), and biological sources where it is synthesized by, for example, methanogenic microorganisms, and industrial or laboratory synthesis. Methane includes pure methane, substantially purified compositions, such as "pipeline quality natural gas" or "dry natural gas", which is 95-98% percent methane; and unpurified compositions, such as "wet natural gas", wherein other hydrocarbons have not yet been removed and methane comprises more than 60% of the composition, and "biogas," which is a mixture of gases produced by the breakdown of organic matter under anaerobic conditions, wherein methane comprises at least 40% or at least 50% of the composition and $CO_2$ comprises up to 50% of the composition.

As used herein, the term "modified" or "recombinant" or "non-natural" refers to an organism, microorganism, cell, nucleic acid molecule, or vector that includes at least one genetic alternation or has been modified by the introduction of a heterologous polynucleotide, or refers to a cell that has been altered such that the expression of an endogenous nucleic acid molecule or gene can be controlled, where such alterations or modifications are introduced by genetic engineering. Genetic alterations include, for example, modifications introducing expressible polynucleotides or nucleic acid molecules encoding proteins or enzymes, other polynucleotide or nucleic acid molecule additions, nucleic acid deletions, nucleic acid substitutions, or other functional disruption of the cell's genetic material. Such modifications include, for example, coding regions and functional fragments thereof for heterologous or homologous polypeptides for the referenced species. Additional modifications include, for example, non-coding regulatory regions in which the modifications alter expression of a gene or operon. Genetic modifications to polynucleotides or nucleic acid molecules encoding enzymes, or functional fragments thereof, can confer a biochemical reaction capability or a metabolic pathway capability to the recombinant cell that is altered from its naturally occurring state. Recombinant methods for expression of heterologous polynucleotides or in microbial organisms are well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999), all of which are incorporated herein by reference. Genetic modifications to nucleic acid molecules encoding enzymes, or functional fragments thereof, can confer a biochemical or metabolic capability to a recombinant cell that is altered from its naturally occurring state.

As used herein, "transformation" refers to the transfer of a polynucleotide (e.g., exogenous or heterologous nucleic acid polynucleotide) into a host. The transformed host may carry the exogenous or heterologous polynucleotide molecule extra-chromosomally or the polynucleotide may integrate into the chromosome. Integration into a host genome and self-replicating vectors generally result in genetically stable inheritance of the transformed nucleic acid molecule. Host cells containing the transformed polynucleotides are referred to as "modified" or "recombinant" or "non-naturally occurring" or "genetically engineered" or "transformed" or "transgenic" cells (e.g. bacteria).

As used herein, the term "endogenous" or "native" refers to a gene, protein, compound or activity that is normally present in a host cell.

As used herein, "heterologous" nucleic acid molecule, polynucleotide, construct or sequence refers to a nucleic acid molecule, polynucleotide or portion of a nucleic acid molecule or polynucleotide that is not native to a host cell or is a polynucleotide with an altered expression as compared to the native expression levels in similar conditions. For example, a heterologous control sequence (e.g., promoter, enhancer) may be used to regulate expression of a native gene or polynucleotide in a way that is different from the way a native gene or polynucleotide is normally expressed in nature or culture. In certain embodiments, heterologous polynucleotides may not be endogenous to a host cell or host genome, but instead may have been added to a host cell by conjugation, transformation, transfection, electroporation, or the like, wherein the added polynucleotide may integrate into the host genome or can exist as extra-chromosomal genetic material (e.g., as a plasmid or other self-replicating vector). In addition, "heterologous" can refer to an enzyme, protein or other activity that is different or altered from that found in a host cell, or is not native to a host cell but instead is encoded by a nucleic acid molecule introduced into the host cell.

The term "homologous" or "homolog" refers to a molecule or activity found in or derived from a host cell, species or strain. For example, a heterologous nucleic acid molecule may be homologous to a native host cell gene, but may have an altered expression level or have a different sequence or both.

In certain embodiments, a heterologous polynucleotide encoding a glycogen catabolism protein, a non-glycogen biosynthesis pathway enzyme, or a control element that regulates the glycogen pathway and or another biosynthetic pathway, or any combination thereof, can be introduced into a host cell on separate nucleic acid molecules, in a polycistronic nucleic acid molecule, in a single nucleic acid molecule encoding a fusion protein, or in any combination thereof. For example, as disclosed herein, a methanotrophic bacterium can be modified to express two or more heterologous or exogenous polynucleotides (e.g., a glycogen catabolism gene, and a gene encoding a non-glycogen biosynthetic pathway enzyme). When two or more heterologous polynucleotides are introduced into a host $C_1$ metabolizing bacteria, such as a methanotrophic bacterium, it is understood that the two or more heterologous polynucleotides can be introduced in a single nucleic acid molecule, for example, in a single vector, in separate vectors, or can be integrated into the host chromosome at a single site or multiple sites, and still be considered two or more heterologous polynucleotides. Thus, the number of referenced heterologous polynucleotides or protein activities refers to the number of encoding polynucleotides or the number of protein activities, not the number of separate nucleic acid molecules introduced into a host cell.

The "percent identity" between two or more nucleic acid sequences is a function of the number of identical positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST).

A "conservative substitution" is recognized in the art as a substitution of one amino acid for another amino acid that has similar properties. Exemplary conservative substitutions are well known in the art (see, e.g., WO 97/09433, page 10, published Mar. 13, 1997; Lehninger, Biochemistry, Second Edition; Worth Publishers, Inc. NY:NY (1975), pp. 71-77; Lewin, Genes IV, Oxford University Press, NY and Cell Press, Cambridge, Mass. (1990), p. 8).

In certain embodiments, it may be desirable to overexpress or increase the expression or activity of a gene or protein involved in production of a desired product (e.g., a desired protein or metabolite). Increased expression or activity includes expression or activity of a gene or protein being increased above the level of a wild-type (native or non-genetically engineered) or parental microorganism. A gene or protein is overexpressed if the expression or activity is in a microorganism where it is not normally expressed or active. A gene or protein is overexpressed if the expression or activity is extended or present longer in the recombinant microorganism than in a wild-type control or reference microorganism. As used herein, "overexpressed" and "overexpression" when referring to a gene or a protein means an increase in expression of the gene or activity of the protein.

In some embodiments, it may be desirable to reduce or inhibit a competing endogenous enzyme activity by mutating the competing endogenous enzyme to delete or attenuate its activity. "Inhibit" or "inhibited," as used herein, refers to an alteration, reduction, down regulation or abrogation, directly or indirectly, in the expression of a target gene or in the activity of a target molecule relative to a control, endogenous or reference molecule, wherein the alteration, reduction, down regulation or abrogation is statistically, biologically, industrially, or clinically significant. For example, inhibition of a target gene in a modified $C_1$ metabolizing bacteria of the instant disclosure may be measured by comparing the expression of the same gene in the parent $C_1$ metabolizing bacteria from which the modified $C_1$ metabolizing bacteria was derived.

A. Genetic Modifications

The present disclosure provides $C_1$ metabolizing bacteria (e.g., methanotrophic or methylotrophic bacteria) that are modified to produce less glycogen, a branched glucose polymer, than the parental bacteria. The modified $C_1$ metabolizing bacteria can have modifications to glycogen biosynthesis genes, glycogen catabolism genes, or combinations thereof. The enzymes required for glycogen biosynthesis and catabolism are highly conserved across bacterial species (Ballicora et al., 2003).

By way of background, glycogen biosynthesis is an ATP-requiring process that utilizes a glucosyl donor for the elongation of the α-1,4-glucosidic chain, which may occur when a carbon source is available in excess and another nutrient required for growth is limiting (e.g. phosphorus, sulfur, or nitrogen). Exemplary glycogen synthesis-related enzymes include phosphoglucomutase (PGM), ADP-glucose pyrophosphorylase (GlgC), glycogen synthase (GlgA, which has two isoforms, GlgA1 and GlgA2), and glycogen branching enzyme (GlgB). Briefly, glycogen biosynthesis begins with PGM converting glucose-6-phosphate into glucose-1-phosphate, which serves as a substrate for ADP-glucose synthesis, which is catalyzed by GlgC. Then GlgA catalyzes the transfer of glucosyl units from ADP-glucose to the elongating chain of linear α-1,4-glucan. Finally, GlgB subsequently cleaves off portions of the glucan and links it to internal glucose molecules in existing chains via α-1,6 glycosidic bonds to form the glycogen molecule.

In contrast, glycogen catabolism (also known as glycogenolysis) is the removal of glucose monomers from a glycogen polymer. Exemplary enzymes involved in glycogen catabolism include glycogen phosphorylase (GlgP), glycogen debranching enzyme (GlgX), and adenosine diphosphate sugar pyrophosphatase (AspP).

Glycogen functions to store carbon (and energy) in many organisms, including bacteria. The function of this polymer may be to enable survival of bacteria during periods of nutrient deprivation (see, e.g., Wilson et al., *FEMS Microbiol Rev.* 34:952, 2010). For example, *Methylococcus* NCIB11083 was found to accumulate up to 35% by weight of glycogen when grown on methane and under conditions of ammonia limitation (see, e.g., Linton and Cripps, *Arch. Microbiol.* 117:41, 1978), and *Methylomicrobium* species have been reported to accumulate upwards of 30% cell dry weight when grown on methanol or under nitrogen limitation (Eshinimaev et al., *Microbiol.* 71:512, 2002). This can have a significant impact on carbon assimilation or conversion efficiency of $C_1$ substrate in an industrial process, such as fermentation.

Knock-Out of Glycogen Synthesis Genes

In certain embodiments, the present disclosure provides a modified $C_1$ metabolizing bacterium, such as methylotrophic or methanotrophic bacteria, having a knock-out of one or more glycogen biosynthesis genes. The one or more glycogen biosynthesis genes that are knocked-out can be, for example, any one or more of genes encoding an ADP-glucose pyrophosphorylase (GlgC), a glycogen synthase (isotype GlgA1 or isotype glgA2), a phosphoglucomutase (PGM), and a glycogen branching enzyme (GlgB).

The present disclosure demonstrates for the first time that a glycogen-null phenotype could be generated in a methanotrophic bacterium by introducing certain single glycogen biosynthesis gene knock-outs. Although *Methylococcus capsulatus* having only a mutated glycogen synthase glgA1 isoform gene showed no alteration in its glycogen phenotype as compared to the unmodified parent *M. capsulatus, M. capsulatus* having a single knock-out of its glycogen synthase glgA2 isoform gene surprisingly resulted in a modified *M. capsulatus* bacteria that produced no, or an undetectable amount of, glycogen as compared to the unmodified parent *M. capsulatus*. Each of these mutants were grown under similar conditions, which included in the presence of methane as a carbon and energy source, with or without nitrogen limitation, and at a high agitation rate (≥1,000 rpm). Glycogen produced by these various bacteria was measured by an iodine staining assay as described, for example, by Goh and Klaenhammer (*Mol. Microbiol.* 89:1187, 2013) (see, also, Example 1 below).

The present disclosure further demonstrates that *Methylococcus capsulatus* containing a mutated ADP-glucose pyrophosphorylase glgC gene (i.e., a single knock-out) surprisingly has a glycogen-null phenotype as compared to the unmodified parent *M. capsulatus*. Even more surprising is *M. capsulatus* having a phosphoglucomutase gene (pgm) knock-out and producing a low or reduced level of glycogen as compared to the unmodified parent *M. capsulatus*. Simply obtaining such ΔglgC and Δpgm mutants was also surprising because there was a possibility that such mutations were going to be lethal in view of their role in nucleotide sugar metabolism and possible unknown role in critical glycosidic bond formation. By way of background, the deletion of pgm or glgC would presumably have prevented activation of 6-carbon sugars with ATP, which was known to be the entry point to particular glycosylation reactions in some bacteria. This type of reaction facilitates glycosidic bond formation to other sugars (resulting in carbohydrates or polysaccharides), amino acids in proteins (resulting in glycoproteins), or lipids (resulting in glycolipids). In particular, polysaccharides and glycolipids form a major component of the outer cell wall in gram-negative bacteria, lipopolysaccharides (LPS). Furthermore, in some pathways, ADP-glucose is a precursor to osmolytes or compatible solutes mannosylglucosylglycerate, glucosylglycerate, and trehalose. The particular osmolyte(s) produced by *M. capsulatus* have not been elucidated yet and, therefore, there was a possibility that a chromosomal knock-out of glgC would be toxic by virtue of an inability to produce a precursor to valuable osmolytes/compatible solutes, in order to respond appropriately to osmotic or salt stress.

Finally, such a glycogen-null phenotype in *M. capsulatus* having a glgA2 or glgC knock-out was also surprising because glycogen could have been formed by the polymerization of UDP-glucose (instead of ADP-glucose). Furthermore, certain bacteria, such as *E. coli*, have alternative pathways to produce ADP-glucose. Therefore it was not known if a single chromosomal knock-out of either glgC or glgA2 gene alone would be sufficient to create a glycogen-null phenotype in *Methylococcus capsulatus*.

In certain embodiments, $C_1$ metabolizing bacteria of this disclosure comprise a chromosomal knock-out of an ADP-glucose pyrophosphorylase gene. ADP-glucose pyrophosphorylase (ADP-Glc PPase, GlgC) catalyzes the reaction: ATP+Glucose-1-phosphate⇔ADP-Glucose+inorganic pyrophosphate. The production of ADP-glucose is a major regulatory step of glycogen biosynthesis (Ballicora et al., *Microbiol. Mol. Biol. Rev.* 67:213, 2003). Exemplary sequences of glgC genes encoded by $C_1$ metabolizing bacteria include *M. fumariolicum* SolV glgC (Accession No. Mfum_1020013); and glgC of *Methylococcus capsulatus* Bath (SEQ ID NO: 1).

In further embodiments, $C_1$ metabolizing bacteria of this disclosure comprise a chromosomal knock-out of a glycogen synthase gene. Glycogen synthase (GlgA, ADP-glucose transglycosylase, which includes two isotypes, GlgA1 and GlgA2) catalyzes the reaction of ADP-glucose and (1,4-α-D-glucosyl)$_n$ to yield ADP and (1,4-α-D-glucosyl)$_{n+1}$. Exemplary sequences of glgA genes encoded by methanotrophic bacteria include *M. fumariolicum* SolV glgA (Accession No. Mfum_1010040); glgA1 of *M. capsulatus* Bath (SEQ ID NO:2); and glgA2 of *M. capsulatus* Bath (SEQ ID NO:3). In certain embodiments, the glycogen synthase gene comprises glgA1, glgA2, or a combination thereof. Many bacteria, including methanotrophic bacteria, express two isoforms of glycogen synthase, known as GlgA1 and GlgA2. GlgA1 is conserved among prokaryotes, whereas GlgA2 is only found in certain bacteria, such as cyanobacteria and methanotrophic bacteria. GlgA2 shares homology with starch synthases III and IV, which are expressed by plants.

In further embodiments, the present disclosure provides a methylotrophic or methanotrophic bacterium modified to have a mutant (e.g., chromosomal knock-out) of an ADP-glucose pyrophosphorylase (glgC) gene, a mutant of a glgA2 isoform of a glycogen synthase gene, or a mutant of both genes. In particular embodiments, the present disclosure provides a modified *Methylococcus capsulatus* comprising a mutated (e.g., chromosomal knock-out) ADP-glucose pyrophosphorylase gene, a mutated glgA2 isoform of a glycogen synthase gene, or both mutated, wherein when cultured under conditions comprising a non-limiting amount of a $C_1$ substrate, the modified *M. capsulatus* produces: (a) at least 30% less glycogen; and/or (b) at least about 5% more crude protein, as compared to the parent (unmodified) *M. capsulatus* cultured under the same conditions. In any of the aforementioned embodiments, the *M. capsulatus* is a *M. capsulatus* Bath.

In certain embodiments, $C_1$ metabolizing bacteria of this disclosure comprise a chromosomal knock-out of a phosphoglucomutase (pgm) gene. Phosphoglucomutase (PGM) is an enzyme that transfers a glucose phosphate group, catalyzing interconversion of glucose 1-phosphate and glucose 6-phosphate. Exemplary sequences of glycogen branching enzyme genes encoded by $C_1$ metabolizing bacteria include *M. fumariolicum* SolV pgm (Accession No. Mfum_550015); pgm-1 of *M capsulatus* Bath (SEQ ID NO:4); and pgm-2 of *M. capsulatus* Bath (SEQ ID NO:5).

In certain embodiments, $C_1$ metabolizing bacteria of this disclosure comprise a chromosomal knock-out of a glycogen branching enzyme (glgB) gene. Glycogen branching enzyme (GlgB) is an enzyme that links glucose moieties (e.g., ADP-glucose or UDP-glucose) to the terminal end of a glycogen chain. Exemplary sequences of glycogen branching enzyme genes encoded by $C_1$ metabolizing bacteria include *M. fumariolicum* SolV glgB (Accession No. Mfum_170041); and glgB of *M. capsulatus* Bath (SEQ ID NO:6).

Various methods for inactivating, knocking-out, or deleting endogenous gene function in $C_1$ metabolizing bacteria may be used. Allelic exchange using suicide vectors to construct deletion/insertional mutants in slow growing $C_1$ metabolizing bacteria have also been described in, for example, Toyama and Lidstrom, *Microbiol.* 144:183, 1998; Stolyar et al., *Microbiol.* 145:1235, 1999; Ali et al., *Microbiol.* 152:2931, 2006; Van Dien et al., *Microbiol.* 149:601, 2003.

In particular embodiments, the chromosomal knock-out of the one or more glycogen synthesis genes is selected from an inactivating substitution, an inactivating deletion, an inactivating insertion, or any combination thereof.

In certain embodiments, the chromosomal knock-out is an in-frame deletion. In particular embodiments, the chromosomal knock-out comprises an in-frame deletion of the glgC gene. SEQ ID NO:7 is an exemplary sequence of a glgC sequence modified to include an in-frame deletion. SEQ ID NO:8 is a wild-type glgC gene locus. In particular embodiments, the chromosomal knock-out comprises an in-frame deletion to the glgA2 gene. SEQ ID NO:9 is an exemplary sequence of a glgA2 sequence modified to include an in-frame deletion.

In certain embodiments, the modified $C_1$ metabolizing bacterium has a single gene knocked out. In certain particular embodiments, the single gene is glgC. In certain particular embodiments, the single gene is glgA2.

In certain embodiments, the modified $C_1$ metabolizing bacterium is glycogen-null. "Glycogen-null" refers to a phenotype wherein the modified bacteria produces at most 20%, such as at most 15%, at most 10%, at most 5%, at most 3%, or at most 1% glycogen produced by the parent $C_1$ metabolizing bacterium cultured under the same conditions. In some embodiments, the glycogen-null phenotype comprises an amount of glycogen production undetectable using, for example, the iodine assay described in Example 1 below. An undetectable amount of glycogen may be, for example, less than 0.01 µg/mL production of glycogen by bacterial culture, as measured by a glycogen enzymatic assay such as the enzymatic assay for glycogen detection described in Example 2.

In certain embodiments, the modified $C_1$ metabolizing bacterium produces at least 20% less, at least 25% less, at least 30% less, at least 35% less, at least 40% less, or at least 45% less glycogen as compared to the parent $C_1$ metabolizing bacterium cultured under the same conditions.

In certain embodiments, the modified $C_1$ metabolizing bacterium produces glycogen at a level that is at most 80%, at most 75%, at most 70%, at most 65%, at most 60%, at most 55%, at most 50%, at most 45%, at most 40%, at most 35%, at most 30%, at most 25%, at most 20%, at most 15%, at most 10%, at most 5% or at most 1% of the glycogen produced by the parent $C_1$ metabolizing bacterium cultured under the same conditions.

In certain embodiments, the modified $C_1$ metabolizing bacterium produces glycogen at a level that is about 0.01% to about 80%, about 0.01% to about 70%, 0.01% to about 60%, about 0.01% to about 50%, 0.01% to about 40%, about 0.01% to about 30%, 0.01% to about 20%, about 0.01% to about 10%, about 0.01% to about 5%, about 0.1% to about 80%, about 0.1% to about 70%, 0.1% to about 60%, about 0.1% to about 50%, 0.1% to about 40%, about 0.1% to about 30%, 0.1% to about 20%, about 0.1% to about 10%, about 0.1% to about 5%, about 1% to about 80%, about 1% to about 70%, 1% to about 60%, about 1% to about 50%, 1% to about 40%, about 1% to about 30%, 1% to about 20%, about 1% to about 10%, or about 1% to about 5% of the glycogen produced by the parent $C_1$ metabolizing bacterium cultured under the same conditions.

In any of the aforementioned embodiments, the $C_1$ metabolizing bacteria is *M. capsulatus*, such as *M. capsulatus* Bath.

Increased Expression of One or More Glycogen Catabolism Genes

In certain embodiments, the modifications include one or more modifications that increase expression of a glycogen catabolism gene. Examples of glycogen catabolism genes include glycogen phosphorylase, glycogen debranching enzyme, and adenosine diphosphate sugar pyrophosphatase.

Certain embodiments include increased expression of a glycogen phosphorylase. Glycogen phosphorylase (GlgP) is an enzyme that releases glucose-1 phosphate from terminal glycosidic bonds of glycogen. Exemplary sequences of glycogen phosphorylase enzyme genes encoded by $C_1$ metabolizing bacteria include *M. fumariolicum* SolV glgP (Accession nr Mfum_1020098); glgP-1 of *M. capsulatus* Bath (SEQ ID NO: 10); and glgP-2 of *M. capsulatus* Bath (SEQ ID NO:11).

Certain embodiments include increased expression of a glycogen debranching enzyme. Glycogen debranching enzyme (GlgX) is an enzyme that catalyzes the removal of glycogen moieties from glycogen polymers. Exemplary sequences of glycogen debranching enzyme genes encoded by $C_1$ metabolizing bacteria include *M. fumariolicum* SolV glgX (Accession nr Mfum_40003); and glgX of *M. capsulatus* Bath (SEQ ID NO:12).

Certain embodiments include increased expression of an adenosine diphosphate sugar pyrophosphatase. Adenosine diphosphate sugar pyrophosphatase (AspP) is an enzyme that cleaves ADP-sugars from molecules such as ADP-glucose, which is a precursor to glycogen. Exemplary sequences of adenosine diphosphate sugar pyrophosphatase genes encoded by $C_1$ metabolizing bacteria include nudF of *Escherichia coli* and aspP of M *capsulatus* Bath (SEQ ID NO:13).

In further embodiments, the increased expression of the one or more glycogen catabolism genes is based on a modification to an endogenous glycogen metabolism gene. Examples of modifications that can increase expression of an endogenous glycogen catabolism enzyme include coding region point mutations that increase expression, use of a heterologous promoter, or mutations that knock-out or decrease function of a negative regulator of a gene encoding a glycogen catabolism enzyme.

In certain embodiments, the increased expression of the one or more glycogen catabolism genes is based on the expression of a heterologous glycogen catabolism gene. The heterologous glycogen catabolism gene may be identical to a glycogen catabolism gene encoded by the $C_1$ metabolizing bacteria (e.g., to increase copy number), or may be a glycogen catabolism gene naturally encoded by another species (e.g., an orthologous glycogen catabolism gene).

In certain embodiments where the modified $C_1$ metabolizing bacterium comprises one or more knock-out of glycogen synthesis genes as well as increased expression of one or more glycogen catabolism genes, the modified $C_1$ metabolizing bacterium produces glycogen at a level at most 80%, at most 75%, at most 70%, at most 65%, at most 60%, at most 55%, at most 50%, at most 45%, at most 40%, at most 35%, at most 30%, at most 25%, at most 20%, at most 15%, at most 10%, at most 5% or at most 1% of the glycogen produced by the parent $C_1$ metabolizing bacterium cultured under the same conditions, such as about 0.01% to about 80%, about 0.01% to about 70%, 0.01% to about 60%, about 0.01% to about 50%, 0.01% to about 40%, about 0.01% to about 30%, 0.01% to about 20%, about 0.01% to about 10%, about 0.01% to about 5%, about 0.1% to about 80%, 0.1% to about 70%, 0.1% to about 60%, about 0.1% to about 50%, 0.1% to about 40%, about 0.1% to about 30%, 0.1% to about 20%, about 0.1% to about 10%, about 0.1% to about 5%, about 1% to about 80%, about 1% to about 70%, 1% to about 60%, about 1% to about 50%, 1% to about 40%, about 1% to about 30%, 1% to about 20%, about 1% to about 10%, or about 1% to about 5% of the glycogen produced by the parent $C_1$ metabolizing bacterium cultured under the same conditions.

Modification to Produce Desired Products

The modified $C_1$ metabolizing bacteria of the present disclosure also provide useful hosts for the production of desired products from a bacterial expression system.

Examples of desired products include an alcohol, an amino acid derived from a tricarboxylic acid cycle (TCA) intermediate (e.g., lysine, tryptophan, methionine, cysteine, and threonine), total amino acids, a nucleotide, an antioxidant, an organic acid, a polyol, an antibiotic, a pigment, a sugar, a vitamin, lactate, pyruvate, or total protein (e.g., crude protein or true protein). The desired product may be any compound or class of compounds that has enhanced production during culturing of the modified $C_1$ metabolizing bacteria as compared to the parent $C_1$ metabolizing bacteria cultured under the same conditions.

"Crude protein," is a protein content measurement that involves measuring the amount of nitrogen in a protein sample.

"True protein," is a protein content calculated based on a crude protein measurement minus the non-protein nitrogen content in a protein sample.

Some embodiments include further modifications to the $C_1$ metabolizing bacteria, for the production of a desired product. These further modifications include modifications to or addition of biosynthesis pathway genes that are related to production of the desired product. In some embodiments, the further modification is a heterologous biosynthesis enzyme gene. In other specific embodiments, the further modification is a modified endogenous biosynthesis enzyme gene.

In particular embodiments, the biosynthesis enzyme is a glycolysis pathway enzyme. A glycolysis pathway enzyme is any enzyme involved in the glycolysis pathway, which converts glucose to pyruvate. Examples of glycolysis pathway enzymes include hexokinase, phosphohexose isomerase, phosphofructo-kinase, aldolase, triosephosphate isomerase, glyceraldehyde-3-P dehydrogenase, phosphoglycerokinase, phosphoglyceromutase, enolase, and pyruvate kinase.

In certain embodiments, the biosynthetic enzyme is an amino acid biosynthesis enzyme. In particular embodiments, the amino acid biosynthesis enzyme is selected from a lysine biosynthesis enzyme, a tryptophan biosynthesis enzyme, a methionine biosynthesis enzyme, a cysteine biosynthesis enzyme, and a threonine biosynthesis enzyme.

In further embodiments, the biosynthetic enzyme is a lysine biosynthesis enzyme. In particular embodiments, the lysine biosynthesis enzyme is selected from: a lysine-sensitive aspartokinase III, an aspartate kinase, an aspartate-semialdehyde dehydrogenase, a dihydrodipicolinate synthase, a dihydrodipicolinate reductase, a 2,3,4,5-tetrahydropyridine-2,6-carboxylate N-succinyltransferase, an acetylornithine/succinyldiaminopimelateaminotransferase, a succinyl-diaminopimelate desuccinylase, a succinyl-diaminopimelate transaminase, a diaminopimelate epimerase, a diaminopimelate dicarboxylase, or any combination thereof.

In still further embodiments, an aspartokinase is further modified to deregulate an endogenous or heterologous aspartokinase activity. Aspartokinase is an enzyme that phosphorylates the amino acid aspartate, which is the first step in the biosynthesis of methionine, lysine, and threonine. Aspartokinases are subject to feedback inhibition, so that high levels of end-product negatively regulate the aspartokinase's activity. In particular embodiments, an aspartokinase mutant that is resistant to feedback inhibition by one or more of lysine, threonine, and methionine is used. An aspartokinase mutant may be a mutant thrA gene, a mutant metL gene, or a mutant lysC gene. The mutations may be spontaneous mutations, random mutations, site specific mutations, or any combination thereof.

In particular embodiments, a deregulated endogenous aspartokinase activity is encoded by a mutant lysC gene, and the mutation is at a threonine binding site. The threonine binding site mutation may be at residue I272, D274, G277, E278, A279, D294, Q298, N372, N374, I375, or any combination thereof. These residue numberings correspond to residue positions encoded by lysC of *Corynebacterium glutamicum* ATCC 13032.

In particular embodiments, the deregulated endogenous aspartokinase activity is encoded by a mutant lysC gene comprising a mutation at a lysine binding site. The lysine binding site mutation may be at residue I291, I293, D294, T361, S381, E382, or any combination thereof. These residue numberings correspond to residue positions encoded by lysC of *Corynebacterium glutamicum* ATCC 13032.

In particular embodiments, the deregulated endogenous aspartokinase activity is encoded by a mutant lysC gene comprising a mutation at a lysine and threonine binding site. The mutation at a lysine and threonine binding site may be at residue D294. This residue numbering corresponds to residue positions encoded by lysC of *Corynebacterium glutamicum* ATCC 13032.

In particular embodiments, the heterologous nucleic acid encoding the biosynthetic enzyme further comprises a heterologous control element that activates or increases expression of one or more biosynthesis enzymes as compared to the biosynthetic enzyme comprising its native control element.

In particular embodiments, the heterologous control element comprises an endogenous control element, a modified endogenous control element, or a heterologous control element. In particular embodiments, the heterologous control element is an exogenous control element that activates or increases expression of the biosynthesis enzyme. In particular embodiments, the heterologous control element is a modified, endogenous promoter that regulates dihydrodipicolinate synthase, wherein the modification increases lysine production.

In particular embodiments, the biosynthetic enzyme is a tryptophan biosynthesis enzyme. In particular embodiments, the tryptophan biosynthesis enzyme is a chorismate-pyruvate lyase, an anthranilate synthase component I, an anthranilate synthase component II, an anthranilate phosphoribosyltransferase, a phosphoribosylanthranilate isomerase, a tryptophan biosynthesis protein, an N-(5'phosphoribosyl) anthranilate isomerase, an indole-3-glycerol phosphate synthase, a tryptophan synthase alpha chain, a tryptophan synthase beta chain, or any combination thereof.

In certain embodiments, the biosynthesis enzyme is a methionine biosynthesis enzyme. In particular embodiments, the methionine biosynthesis enzyme is selected from a homoserine 0-acetyltransferase, a homoserine 0-succinyltransferase (e.g., MetA and MetXW), a cystathionine gamma-synthase, a protein MalY, a cystathionine beta-lyase, a B12-dependent methionine synthase, a 5-methyltetrahydropteroyltriglutamate-homocysteine S-methyltransferase, O-acetylhomoserine aminocarboxypropyltransferase (e.g., MetX), or any combination thereof.

In certain embodiments, the biosynthesis enzyme is a cysteine biosynthesis enzyme. In particular embodiments, the cysteine biosynthesis enzyme is a serine acetyltransferase, a cysteine synthase A, a cysteine synthase B, or any combination thereof.

In certain embodiments, the biosynthesis enzyme is a threonine biosynthesis enzyme. In particular embodiments, the threonine biosynthesis enzyme is an aspartate transaminase, a PLP-dependent aminotransferase, an aspartate aminotransferase, an aspartate kinase, an aspartate-semialdehyde dehydrogenase, a homoserine dehydrogenase, a homoserine kinase, a threonine synthase, or any combination thereof.

In certain embodiments, the modified $C_1$ metabolizing bacteria produces a greater amount of the desired product during culturing, as compared to the parent $C_1$ metabolizing bacteria cultured under the same conditions. In certain embodiments, the modified $C_1$ metabolizing bacterium produces at least 5%, at least 10%, at least 15%, at least 20%, at least 25%, at least 30%, at least 35%, at least 40%, at least 45%, at least 50%, at least 60%, at least 70%, at least 80%, at least 90% or at least 100% more, such as 105% to 900%, 110% to 800%, 115% to 700%, 120% to 600%, or 125% to 500% of the desired product during culturing, as compared to the parent $C_1$ metabolizing bacterium cultured under the same conditions. In certain particular embodiments, the modified $C_1$ metabolizing bacterium produces at least 5%, at least 10%, at least 15%, at least 20%, at least 25%, at least 30%, at least 35%, at least 40%, at least 45%, at least 50%, at least 60%, at least 70%, at least 80%, at least 90% or at least 100% more, such as 105% to 900%, 110% to 800%, 115% to 700%, 120% to 600%, or 125% to 500% of crude protein during culturing, as compared to the parent $C_1$ metabolizing bacterium cultured under the same conditions. In certain particular embodiments, the modified $C_1$ metabolizing bacterium produces at least 5%, at least 10%, at least 15%, at least 20%, at least 25%, at least 30%, at least 35%, at least 40%, at least 45%, at least 50%, at least 60%, at least 70%, at least 80%, at least 90% or at least 100% more, such as 105% to 900%, 110% to 800%, 115% to 700%, 120% to 600%, or 125% to 500% of one or more amino acids derived from TCA intermediates or total amino acids during culturing, as compared to the parent $C_1$ metabolizing bacterium cultured under the same conditions.

Codon Optimization

Expression of recombinant or heterologous proteins is often difficult outside their original host. For example, variation in codon usage bias has been observed across different species of bacteria (Sharp et al., *Nucl. Acids. Res.* 33:1141, 2005). Over-expression of recombinant proteins even within their native host may also be difficult. In certain embodiments of the invention, nucleic acids (e.g., nucleic acids encoding fatty acid elongation enzymes) that are to be introduced into host methanotrophic bacteria as described herein may undergo codon optimization to enhance protein expression. Codon optimization refers to alteration of codons in genes or coding regions of polynucleotides for transformation of a methanotrophic bacterium to reflect the typical codon usage of the host bacteria species without altering the polypeptide for which the DNA encodes. Codon optimization methods for optimum gene expression in heterologous hosts have been previously described (see, e.g., Welch et al., *PLoS One* 4:e7002, 2009; Gustafsson et al., *Trends Biotechnol.* 22:346, 2004; Wu et al., *Nucl. Acids Res.* 35:D76, 2007; Villalobos et al., *BMC Bioinformatics* 7:285, 2006; U.S. Patent Application Publication Nos. US 2011/0111413; US 2008/0292918; disclosure of which are incorporated herein by reference, in their entirety).

Transformation Methods

Any of the modified $C_1$ metabolizing bacteria described herein may be transformed to comprise at least one exogenous polynucleotide to provide the host bacterium with a new or enhanced activity (e.g., enzymatic activity) or may be genetically modified to remove or substantially reduce an endogenous gene function using a variety of methods known in the art.

Transformation refers to the transfer of a polynucleotide (e.g., exogenous polynucleotide) into the genome of a host cell, resulting in genetically stable inheritance. Host cells containing the transformed nucleic acid molecules are referred to as "non-naturally occurring" or "recombinant" or "transformed" or "transgenic" cells.

Expression systems and expression vectors useful for the expression of heterologous polynucleotides in $C_1$ metabolizing bacteria.

Electroporation of $C_1$ metabolizing bacteria has been previously described in Toyama et al., *FEMS Microbiol. Lett.* 166:1, 1998; Kim and Wood, *Appl. Microbiol. Biotechnol.* 48:105, 1997; Yoshida et al., *Biotechnol. Lett.* 23:787, 2001, and U.S. Patent Application Publication No. US 2008/0026005.

Bacterial conjugation, which refers to a particular type of transformation involving direct contact of donor and recipient cells, is more frequently used for the transfer of nucleic acids into $C_1$ metabolizing bacteria. Bacterial conjugation involves mixing "donor" and "recipient" cells together in close contact with each other. Conjugation occurs by formation of cytoplasmic connections between donor and recipient bacteria, with unidirectional transfer of newly synthesized donor polynucleotides into the recipient cells. A recipient in a conjugation reaction is any cell that can accept nucleic acids through horizontal transfer from a donor bacterium. A donor in a conjugation reaction is a bacterium that contains a conjugative plasmid, conjugative transposon, or mobilized plasmid. The physical transfer of the donor plasmid can occur through a self-transmissible plasmid or with the assistance of a "helper" plasmid. Conjugations involving $C_1$ metabolizing bacteria have been previously described in Stolyar et al., *Mikrobiologiya* 64:686, 1995; Motoyama et al., *Appl. Micro. Biotech.* 42:67, 1994; Lloyd et al., *Arch. Microbiol.* 171:364, 1999; and Odom et al., PCT Publication No. WO 02/18617; Ali et al., *Microbiol.* 152:2931, 2006.

Expression of heterologous polynucleotides in $C_1$ metabolizing bacteria is known in the art (see, e.g., U.S. Pat. No. 6,818,424; U.S. Patent Application Publication No. US 2003/0003528). Mu transposon based transformation of methylotrophic bacteria has been described (Akhverdyan et al., *Appl. Microbiol. Biotechnol.* 91:857, 2011). A mini-Tn7 transposon system for single and multicopy expression of heterologous genes without insertional inactivation of host genes in *Methylobacterium* has been described (U.S. Patent Application Publication No. US 2008/0026005).

Suitable homologous or heterologous promoters for high expression of heterologous polynucleotides may be utilized. For example, U.S. Pat. No. 7,098,005 describes the use of promoters that are highly expressed in the presence of methane or methanol for heterologous gene expression in $C_1$ metabolizing bacteria. Additional promoters that may be used include deoxy-xylulose phosphate synthase methanol dehydrogenase operon promoter (Springer et al., *FEMS Microbiol. Lett.* 160:119, 1998); the promoter for PHA synthesis (Foellner et al., *Appl. Microbiol. Biotechnol.* 40:284, 1993); or promoters identified from a native plasmid in methylotrophs (European Patent No. EP 296484). Non-native promoters include the lac operon Plac promoter (Toyama et al., *Microbiol.* 143:595, 1997) or a hybrid promoter such as Ptrc (Brosius et al., *Gene* 27:161, 1984). In certain embodiments, promoters or codon optimization are used for high constitutive expression of heterologous polynucleotides encoding one or more glycogen pathway genes (e.g., a glycogen catabolism gene), and or one or more polynucleotides encoding biosynthetic enzymes for producing a desired product. Regulated expression of a heterologous polynucleotide in the modified $C_1$ metabolizing bacteria may also be utilized. In particular, regulated expression of heterologous polynucleotides encoding glycogen synthesis genes may be desirable. It is possible that in the absence of glycerol (e.g., during growth on methane as a carbon source), for the glycerol utilization pathway to run in reverse, resulting in secretion of glycerol from the bacteria, thereby lowering growth rate. Controlled expression of polynucleotides encoding glycerol utilization pathway enzymes in response to the presence of glycerol may optimize bacterial growth in a variety of carbon source conditions. For example, an inducible/regulatable system of recombinant protein expression in $C_1$ metabolizing bacteria, as described in U.S. Patent Application Publication No. US 2010/0221813, may be used. Regulation of glycerol utilization genes in bacteria is well established (Schweizer and Po, *J. Bacteriol.* 178:5215, 1996; Abram et al., *Appl. Environ. Microbiol.* 74:594, 2008; Darbon et al., *Mol. Microbiol.* 43:1039, 2002; Weissenborn et al., *J. Biol. Chem.* 267:6122, 1992). Glycerol utilization regulatory elements may also be introduced or inactivated in host $C_1$ metabolizing bacteria for desired expression levels of heterologous polynucleotides encoding glycerol utilization pathway enzymes.

Methods of screening are disclosed in Brock, supra. Selection methods for identifying allelic exchange mutants are known in the art (see, e.g., U.S. Patent Appl. Publication No. US 2006/0057726, Stolyar et al., *Microbiol.* 145:1235, 1999; and Ali et al., *Microbiol.* 152:2931, 2006.

B. $C_1$ Metabolizing Bacteria

In certain embodiments, the present disclosure provides $C_1$ metabolizing bacteria modified to produce less glycogen and/or more desired product(s), such as proteins or metabolites.

As used herein, "$C_1$ metabolizing bacteria" or "$C_1$ metabolizing bacterium" refers to any bacterium having the ability to use a $C_1$ substrate as a source of energy or as its primary source of energy or as its sole source of energy and biomass, and may or may not use other carbon substrates (such as sugars and complex carbohydrates) for energy and biomass. For example, a $C_1$ metabolizing bacteria may oxidize a $C_1$ substrate comprised of, for example, methane, natural gas, or methanol. Exemplary $C_1$ metabolizing bacteria include, for example, *Methylomonas, Methylobacter, Methylococcus, Methylosinus, Methylomicrobium, Methanomonas, Methylophilus, Methylobacillus, Methylobacterium, Methylocystis, Methylocella, Methanomonas, Methylacidiphilum,* or *Methylocapsa.*

In certain embodiments, a $C_1$ metabolizing bacterium is an "obligate $C_1$ metabolizing bacterium," meaning its sole source of energy is from a $C_1$ substrate. In further embodiments, a $C_1$ metabolizing bacterium is a "facultative $C_1$ metabolizing bacterium" that are naturally capable of growing on substrates other than a $C_1$ substrate.

In certain embodiments, a $C_1$ metabolizing bacterium is a methanotrophic bacterium or a methylotrophic bacterium.

As used herein, the term "methylotroph" or "methylotrophic bacterium" refers to any bacterium capable of oxidizing methyl-containing organic compounds (e.g., methanol) that do not contain carbon-carbon bonds. Exemplary methylotrophs include *Methylobacterium extorquens, Methylobacterium radiotolerans, Methylobacterium populi, Methylobacterium chloromethanicum, Methylobacterium nodulans,* or a high-growth variant thereof.

In certain other embodiments, the methylotrophic bacterium is an "obligate methylotrophic bacterium," which refers to bacteria that are limited to the use of methyl-containing compounds (e.g., methanol), or other $C_1$ substrates comprising such compounds, for the generation of energy. In certain embodiments, a methylotrophic bacterium may be a methanotroph. As used herein, the term "methanotrophic bacterium" or "methanotrophic bacteria" refers to bacteria capable of utilizing methane or a $C_1$ substrate comprising methane (e.g., natural gas), as its primary or sole carbon and energy source.

Methanotrophic bacteria are classified into three groups based on their carbon assimilation pathways and internal membrane structure: type I (gamma proteobacteria), type II (alpha proteobacteria, and type X (gamma proteobacteria). Type I methanotrophs use the ribulose monophosphate (RuMP) pathway for carbon assimilation whereas type II methanotrophs use the serine pathway. Type X methanotrophs use the RuMP pathway but also express low levels of enzymes of the serine pathway. Methanotrophic bacteria include obligate methanotrophs, which can only utilize $C_1$ substrates for carbon and energy sources, and facultative methanotrophs, which naturally have the ability to utilize some multi-carbon substrates as a sole carbon and energy source.

Exemplary methanotrophic bacteria include *Methylococcus capsulatus* Bath, *Methylomonas methanica* 16a, *Methylosinus trichosporium* OB3b, *Methylosinus sporium*, *Methylocystis parvus*, *Methylomonas methanica*, *Methylomonas albus*, *Methylobacter capsulatus*, *Methylomonas* sp AJ-3670, *Methylacidiphilum infernorum*, *Methylobacter capsulatus* Y, *Methylobacterium organophilum*, *Methylomonas* sp. AJ-3670, *Methylomicrobium alcahphilum*, *Methylocella silvestris*, *Methylibium petroleiphilum*, *Methylobacterium extorquens*, *Methylobacterium radiotolerans*, *Methylobacterium populi*, *Methylobacterium chloromethanicum*, *Methylobacterium nodulans*, *Methylocella palustris*, *Methylocella tundra*, *Methylocystis daltona* SB2, *Methylocystis bryophila*, *Methylocapsa aurea* KYG, *Methylacidiphilum fumariolicum*, *Methyloacida kamchatkensis*, *Methylocella palustris*, *Methylocella tundra*, *Methylomicrobium buryatense* 5G, *Methylocapsa auream*, or a high-growth variant thereof.

In certain embodiments, a methanotrophic bacterium may be an "obligate methanotrophic bacterium," which refers to a bacterium that can only utilize methane as a carbon and energy source.

In certain other embodiments, a methanotrophic bacterium may be a "facultative methanotrophic bacterium," which refers to a bacterium that is naturally able to use substrates other than methane, such as acetate, pyruvate, succinate, malate, or ethanol, as their sole carbon and energy source.

Exemplary obligate methanotrophic bacteria include, for example, *Methylococcus capsulatus* Bath, *Methylosinus trichosporium* OB3b, *Methylomonas* 16a, *Methylosinus sporium*, *Methylocystis parvus*, *Methylomonas methanica*, *Methylomonas albus*, *Methylobacter capsulatus*, *Methylomonas* sp. AJ-3670, *Methylomicrobium alcahphilum*, and high growth variants thereof. Facultative methanotrophic bacteria include, for example, some species of *Methylocella*, *Methylocystis*, and *Methylocapsa* (e.g., *Methylocella silvestris*, *Methylocella palustris*, *Methylocella tundrae*, *Methylocystis daltona* SB2, *Methylocystis bryophila*, and *Methylocapsa aurea* KYG), *Methylobacterium organophilum* (e.g., ATCC 27,886), and high growth variants thereof.

In certain embodiments, a $C_1$ substrate feedstock for a $C_1$ metabolizing bacteria as described herein comprises methane, methanol, formaldehyde, formic acid or a salt thereof, carbon monoxide, carbon dioxide, a methylamine, a methylthiol, a methylhalogen, natural gas, or unconventional natural gas. In certain embodiments, modified $C_1$ metabolizing bacteria are capable of converting natural gas, unconventional natural gas, or syngas (e.g., syngas comprising methane) into a desired product as described herein.

The term "parental" or "wild-type" refers herein to $C_1$ metabolizing bacteria that are an ancestor of a genetically modified or recombinant $C_1$ metabolizing bacteria of the present disclosure. A parental $C_1$ metabolizing bacteria may be a wild-type $C_1$ metabolizing bacteria, or may be an altered or mutated form of wild-type $C_1$ metabolizing bacteria.

Any of the aforementioned $C_1$ metabolizing bacteria may also have undergone strain adaptation under selective conditions to produce variants with improved properties for reduced glycogen production and/or improved properties for production of a desired product, before or after knock-out of the one or more glycogen synthesis pathway genes. Improved properties may include increased growth rate, yield of desired products (e.g., a desired protein product), or tolerance to process or culture contaminants. In particular embodiments, a high growth variant modified $C_1$ metabolizing bacteria comprises a host bacteria that is capable of growing on a methane feedstock as a primary carbon and energy source and that possesses a faster exponential phase growth rate (i.e., shorter doubling time) than its parent, reference, or wild-type bacteria (see, e.g., U.S. Pat. No. 6,689,601).

Each of the bacteria of this disclosure may be grown as an isolated culture, with a heterologous organism that may aid with growth, or one or more of these bacteria may be combined to generate a mixed culture.

In any of the aforementioned embodiments, a $C_1$ metabolizing bacterium is *Methylococcus capsulatus*, such as *Methylococcus capsulatus* Bath.

C. Methods of Culturing Glycogen-Null $C_1$ Metabolizing Bacteria

The modified $C_1$ metabolizing bacteria described herein (e.g., *Methylococcus capsulatus* Bath) may be cultured under conditions that lead to less glycogen production or more crude protein as compared to the parent $C_1$ metabolizing bacteria cultured under the same conditions, and may be cultured to produce desired products (e.g., proteins, metabolites).

In some embodiments, the modified $C_1$ metabolizing bacteria produce glycogen at a level at most 80%, at most 75%, at most 70%, at most 65%, at most 60%, at most 55%, at most 50%, at most 45%, at most 40%, at most 35%, at most 30%, at most 25%, at most 20%, at most 15%, at most 10%, at most 5% or at most 1% of the glycogen produced by the parent $C_1$ metabolizing bacterium cultured under the same conditions, such as about 0.01% to about 80%, about 0.01% to about 70%, 0.01% to about 60%, about 0.01% to about 50%, 0.01% to about 40%, about 0.01% to about 30%, 0.01% to about 20%, about 0.01% to about 10%, about 0.01% to about 5%, about 0.1% to about 80%, about 0.1% to about 70%, 0.1% to about 60%, about 0.1% to about 50%, 0.1% to about 40%, about 0.1% to about 30%, 0.1% to about 20%, about 0.1% to about 10%, about 0.1% to about 5%, about 1% to about 80%, about 1% to about 70%, 1% to about 60%, about 1% to about 50%, 1% to about 40%, about 1% to about 30%, 1% to about 20%, about 1% to about 10%, or about 1% to about 5% of the glycogen produced by the parent $C_1$ metabolizing bacterium cultured under the same conditions.

In particular embodiments, the culture conditions include the presence of a non-limiting amount of a $C_1$ substrate. $C_1$ substrate may refer to an organic compound with no carbon-carbon bonds, which may be utilized by certain organisms for energy. Examples of $C_1$ substrates include formate, formaldehyde, methane, methanol, and carbon monoxide. In particular embodiments, the $C_1$ substrate is methane or methanol.

A "non-limiting amount of a $C_1$ substrate" as used herein refers to an amount a $C_1$ substrate (e.g., methane or methanol) that provides a cultured bacterium enough carbon as an energy source such that the growth of the bacterium is not impeded based on the amount of the $C_1$ substrate (e.g., as determined by measuring optical density of culture or dry cell weight production). In certain embodiments, a non-limiting amount of methane comprises at least 50 ml/min, at least 80 mL/min, at least 90 mL/min, at least 100 mL/min, 50 mL/min to 500 mL/min, 50 mL/min to 150 mL/min, 80 mL/min to 250 mL/min, 90 mL/min to 200 mL/min, or 100 mL/min to 150 mL/min, per 1.5 L of $C_1$ metabolizing bacteria in culture. In certain embodiments, a non-limiting amount of methanol comprises at least 200 mg/hour, at least 500 mg/hour, at least 1 g/hour, 200 mg/hour to 50 g/hour, 500 mg/hour to 25 g/hour, or 1 g/hour to 20 g/hour, per 1.5 L of $C_1$ metabolizing bacteria in culture.

Some embodiments include methods of culturing a modified $C_1$ metabolizing bacterium disclosed herein to produce a desired product.

In certain embodiments, the modified $C_1$ metabolizing bacterium is cultured for a time sufficient to produce a desired product. The time period may be at least: one hour, two hours, three hours, four hours, five hours, six hours, seven hours, eight hours, nine hours, ten hours, eleven hours, twelve hours, one day, two days, three days, four days, five days, one week, or longer.

In certain embodiments, the quantity of the desired product is greater than a quantity of the desired product produced by the parental bacteria cultured under the same conditions.

The culture condition may include the presence of a limiting amount of a nutrient or metabolite required for growth (e.g., as determined by measuring optical density of culture or dry cell weight production). In certain embodiments, the culture condition comprises a limited availability of a nutrient required for growth relative to the availability of carbon. For example, under such conditions, a modified $C_1$ metabolizing bacteria may have a higher rate of carbon assimilation that exceeds the ability the modified $C_1$ metabolizing bacteria to produce biomass due to the limited availability of another, non-carbon nutrient necessary for biosynthesis of one or more cellular components of the biomass (e.g., amino acid).

In particular embodiments, a limiting amount of a nutrient or metabolite required for growth comprises a limiting amount of nitrogen, sulfur, phosphorous, and/or oxygen, which optionally is in relation to the amount of carbon available for assimilation or conversion. In particular embodiments, a limiting amount of nitrogen comprises a limiting amount of nitrate, ammonium, nitrogen gas, or any combination thereof. For example, a culturing condition having a limiting amount of nitrogen may include nitrogen fixation ranging from about 10% to about 90%, from about 20% to about 80%, or from about 30% to about 70%. In certain embodiments, a limited amount of nitrogen can include nitrogen fixing conditions, when the nitrogen feed rate is below levels found in balanced culture media. In particular embodiments, a culture condition comprises a nitrogen source (e.g., $HNO_3$) at a concentration that is low enough to stimulate glycogen production by a wild-type $C_1$ metabolizing bacteria (e.g., *M. capsulatus* Bath) when cultured with a non-limiting amount of carbon. In further particular embodiments, a limiting amount of nitrogen may be a feed rate of $HNO_3$ (e.g., at a concentration of 0.1-1M, or 1M, 0.9M. 0.8M. 0.7M, 0.6M, 0.5M, 0.4M, 0.3M, 0.2M, or 0.1M) of less than 60 g/h, less than 50 g/h, less than 40 g/h, less than 30 g/h, less than 25 g/h, less than 20 g/h, less than 15 g/h, or less than 10 g/h. In further particular embodiments, a limiting amount of nitrogen may be a feed rate of $NH_4$ (e.g., at a concentration of 0.1-1M, or 1M, 0.9M. 0.8M. 0.7M, 0.6M, 0.5M, 0.4M, 0.3M, 0.2M, or 0.1M) of less than 90 g/h, less than 80 g/h, less than 70 g/h, less than 60 g/h, less than 50 g/h, less than 40 g/h, less than 30 g/h, less than 20 g/h, less than 10 g/h, or less than 5 g/h, such as at a rate in the range from 90 g/h to 0.5 g/h.

The culture conditions may include the presence of a limiting amount of a $C_1$ substrate, such as methane or methanol.

In certain embodiments, the desired product may be a metabolite selected from an alcohol, an amino acid, a nucleotide, an antioxidant, an organic acid, a polyol, an antibiotic, a pigment, a sugar, and a vitamin, or any combination thereof.

In certain embodiments, the desired product is a protein or total protein.

In certain embodiments, the desired product is pyruvate, lactate, an amino acid derived from a tricarboxylic acid cycle (TCA) intermediate, or any combination thereof.

In some embodiments, the modified $C_1$ metabolizing bacteria produce more crude protein than the parental $C_1$ metabolizing bacteria cultured under the same conditions. In particular embodiments, the modified $C_1$ metabolizing bacteria produce at least 5% more, at least 10% more, at least 15% more, or at least 20% more crude protein than the parental $C_1$ metabolizing bacteria cultured under the same conditions.

In certain embodiments, a desired product is produced during a specific phase of cell growth (e.g., lag phase, log phase, stationary phase, or death phase). In some embodiments, modified methanotrophic bacteria as provided herein are cultured to a low to medium cell density ($OD_{600}$) and then production of a desired product is initiated. In some embodiments, a desired product is produced while the modified methanotrophic bacteria are no longer dividing or dividing very slowly. In some embodiments, a desired product is produced only during stationary phase. In some embodiments, a desired product is produced during log phase and stationary phase.

When culturing is done in a liquid culture medium, the gaseous $C_1$ substrates may be introduced and dispersed into a liquid culture medium using any of a number of various known gas-liquid phase systems as described in more detail herein below. When culturing is done on a solid culture medium, the gaseous $C_1$ substrates are introduced over the surface of the solid culture medium.

Conditions sufficient to produce a desired product include culturing the modified methanotrophic bacteria at a temperature in the range of about 0° C. to about 55° C. In some embodiments, the culture temperature is in the range of about 25° C. to about 50° C. In some embodiments, the culture temperature is in the range of about 37° C. to about 50° C., and may be in the range of about 37° C. to about 45° C. Other conditions sufficient to produce a desired product include culturing the modified methanotrophs at a pH in the range of about 6 to about 9, or in the range of about 7 to about 8.

In certain embodiments, modified methanotrophic bacteria provided herein produce a desired product at about 0.001 g/L of culture to about 500 g/L of culture. In some embodiments, the amount of desired product produced is about 1 g/L of culture to about 100 g/L of culture. In some embodiments, the amount of desired product produced is about 0.001 g/L to about 5 g/L, about 0.001 g/L to about 100 g/L, about 0.01 g/L to about 5 g/L, about 0.01 g/L to about 100 g/L, about 0.1 g/L to about 50 g/L, about 0.1 g/L to about 500 g/L, about 1 g/L to about 50 g/L, about 1 g/L to about 500 g/L, about 10 g/L to about 100 g/L, or about 100 g/L to about 500 g/L.

A variety of culture methodologies may be used for modified methanotrophic bacteria described herein. For example, methanotrophic bacteria may be grown by batch culture or continuous culture methodologies. In certain embodiments, the cultures are grown in a controlled culture unit, such as a fermenter, bioreactor, hollow fiber membrane bioreactor, or the like. Other suitable methods include classical batch or fed-batch culture or continuous or semi-continuous culture methodologies. In certain embodiments, the cultures are grown in a controlled culture unit, such as a fermenter, bioreactor, hollow fiber membrane bioreactor, and the like.

A classical batch culturing method is a closed system where the composition of the media is set at the beginning of the culture and not subject to external alterations during the culture process. Thus, at the beginning of the culturing process, the media is inoculated with the desired mutant methanotrophic bacteria and growth or metabolic activity is permitted to occur without adding anything further to the system. Typically, however, a "batch" culture is batch with respect to the addition of the methanotrophic substrate and attempts are often made at controlling factors such as pH and oxygen concentration. In batch systems, the metabolite and biomass compositions of the system change constantly up to the time the culture is terminated. Within batch cultures, cells moderate through a static lag phase to a high growth logarithmic phase and finally to a stationary phase where growth rate is diminished or halted. If untreated, cells in the stationary phase will eventually die. Cells in logarithmic growth phase are often responsible for the bulk production of end product or intermediate in some systems. Stationary or post-exponential phase production can be obtained in other systems.

The Fed-Batch system is a variation on the standard batch system. Fed-Batch culture processes comprise a typical batch system with the modification that the methanotrophic substrate is added in increments as the culture progresses. Fed-Batch systems are useful when catabolite repression is apt to inhibit the metabolism of the cells and where it is desirable to have limited amounts of the $C_1$ substrate in the media. Measurement of the actual substrate concentration in Fed-Batch systems is difficult and is therefore estimated on the basis of the changes of measureable factors, such as pH, dissolved oxygen, and the partial pressure of waste gases such as $CO_2$. Batch and Fed-Batch culturing methods are common and known in the art (see, e.g., Thomas D. Brock, Biotechnology: A Textbook of Industrial Microbiology, 2$^{nd}$ Ed. (1989) Sinauer Associates, Inc., Sunderland, Mass.; Deshpande, *Appl. Biochem. Biotechnol.* 36:227, 1992, which methods are incorporated herein by reference in their entirety).

Continuous cultures are "open" systems where a defined culture media is added continuously to a bioreactor and an equal amount of conditioned media is removed simultaneously for processing. Continuous cultures generally maintain the cells at a constant high liquid phase density where cells are primarily in logarithmic phase growth. Alternatively, continuous culture may be practiced with immobilized cells where the methanotrophic substrate and nutrients are continuously added and valuable products, by-products, and waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limited nutrient, such as the $C_1$ substrate or nitrogen level, at a fixed rate and allow all other parameters to modulate. In other systems, a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art.

Liquid phase bioreactors (e.g., stirred tank, packed bed, one liquid phase, two liquid phase, hollow fiber membrane) are well known in the art and may be used for growth of modified microorganisms and biocatalysis.

By using gas phase bioreactors, substrates for bioproduction are absorbed from a gas by modified microorganisms, cell lysates or cell-free fractions thereof, rather than from a liquid. Use of gas phase bioreactors with microorganisms is known in the art (see, e.g., U.S. Pat. Nos. 2,793,096; 4,999,302; 5,585,266; 5,079,168; and 6,143,556; U.S. Statutory Invention Registration H1430; U.S. Pat. Appl. Pub. No. US 2003/0032170; Emerging Technologies in Hazardous Waste Management III, 1993, eds. Tedder and Pohland, pp. 411-428, all of which are incorporated herein by reference). Exemplary gas phase bioreactors include single pass system, closed loop pumping system, and fluidized bed reactor. By utilizing gas phase bioreactors, methane or other gaseous substrates is readily available for bioconversion by polypeptides with, for example, monooxygenase activity. In certain embodiments, methods for converting a gas into a desired product are performed in gas phase bioreactors. In further embodiments, methods for converting a gas into a desired product are performed in fluidized bed reactors. In a fluidized bed reactor, a fluid (i.e., gas or liquid) is passed upward through particle bed carriers, usually sand, granular-activated carbon, or diatomaceous earth, on which microorganisms can attach and grow. The fluid velocity is such that particle bed carriers and attached microorganisms are suspended (i.e., bed fluidization). The microorganisms attached to the particle bed carriers freely circulate in the fluid, allowing for effective mass transfer of substrates in the fluid to the microorganisms and increased microbial growth. Exemplary fluidized bed reactors include plug-flow reactors and completely mixed reactors. Uses of fluidized bed reactors with microbial biofilms are known in the art (e.g., Pfluger et al., *Bioresource Technol.* 102:9919, 2011; Fennell et al., *Biotechnol, Bioengin.* 40:1218, 1992; Ruggeri et al., *Water Sci. Technol.* 29:347, 1994; U.S. Pat. Nos. 4,032,407; 4,009,098; 4,009,105; and 3,846,289, all of which are incorporated herein by reference).

Methanotrophic bacteria described in the present disclosure may be grown as an isolated pure culture, with a heterologous non-methanotrophic bacteria that may aid with growth, or one or more different strains or species of methanotrophic bacteria may be combined to generate a mixed culture.

In alternative embodiments, methods described herein use modified methanotrophic bacteria of the present disclosure or cell lysates thereof immobilized on, within, or behind a solid matrix. In further embodiments, the non-naturally occurring methanotrophs of the present disclosure, cell lysates or cell-free extracts thereof are in a substantially non-aqueous state (e.g., lyophilized). Modified microorganisms, cell lysates or cell-free fractions thereof are temporarily or permanently attached on, within, or behind a solid matrix within a bioreactor. Nutrients, substrates, and other required factors are supplied to the solid matrices so that the cells may catalyze the desired reactions. Modified microorganisms may grow on the surface of a solid matrix (e.g., as a biofilm). Modified microorganisms, cell lysates or cell-free fractions derived thereof may be attached on the surface or within a solid matrix without cellular growth or in a non-living state. Exemplary solid matrix supports for microorganisms include polypropylene rings, ceramic bio-rings, ceramic saddles, fibrous supports (e.g., membrane), porous glass beads, polymer beads, charcoal, activated carbon, dried silica gel, particulate alumina, Ottawa sand, clay, polyurethane cell support sheets, and fluidized bed particle carrier (e.g., sand, granular-activated carbon, diatomaceous earth, calcium alginate gel beads).

EXAMPLES

Example 1

Small Scale Analysis of Glycogen Production

In order to evaluate the phenotype of methanotrophic bacteria with chromosomal deletion mutants in glycogen biosynthesis genes, *Methylococcus capsulatus* Bath deletion mutants ΔglgA2 and ΔglgC were grown under glycogen production-triggering conditions in a small scale (2.5 mL) growth format. One objective was to demonstrate that the targeted glgA2 and glgC knockouts did not produce glycogen under typically triggering conditions. An iodine assay was used to qualitatively evaluate the glycogen content of the wild-type control and the ΔglgA2 and ΔglgC mutants. The iodine assay is a common technique for detecting glycogen or starch and is based upon the intercalation of iodine molecules into the sugar polymer backbone. Upon this intercalation, the glycogen-containing material stains a dark brownish-black, indicating the presence of glycogen. The iodine partitions easily into the cell and the assay is nearly instantaneous. An iodine assay protocol is described in detail in Goh and Klaenhammer, *Mol. Microbiol.* 89:1187, 2013. The strains were first grown with a non-*limiting amount of nitrate in* 2.5 ml of media for 48 hours. They were then used to inoculate either non-limiting or nitrate-free media to an OD of 1.0. After four hours, 200 μl samples of each growth condition were transferred to a microtiter plate and 20 μl of Lugol's Iodine Solution (an aqueous solution of iodine and potassium iodide) was added to each well. The cultures were centrifuged and washed once with 200 μl fresh medium, then pelleted again.

FIG. 1A shows centrifuged cell pellets of two strains (three clones each), the wild-type control (wt) and the MCA2606 (ΔglgA2) deletion mutant, after staining with iodine. In the nitrate-free condition, the wild-type control produces glycogen and stains dark brown/black. In the presence of nitrate, minimal glycogen is produced and the wild-type cells are a paler orange color. By contrast, the stained mutant exhibits the paler orange color under both conditions, indicating the absence of glycogen. FIG. 1B shows the presence of glycogen in a wild-type strain under nitrate-free conditions, and the absence of glycogen in the MCA1474 deletion mutant (ΔglgC) under nitrate-free conditions. These data qualitatively demonstrated the glycogen-null phenotype in both the ΔglgA2 and ΔglgC mutants.

Example 2

Growth of Glycogen-Null *M. Capsulatus* Bath in a Continuous Culture System

In order to determine the impact of the glycogen-null phenotype on cells grown in 2 L growth format with methanol as the carbon and energy source, the wild-type and the MCA1474 deletion mutant (ΔglgC, labeled G680, Glycogen (−) in Table 1) were grown in 2 L vessels in continuous fermentation. An objective of the experiment was to demonstrate the ability to produce less glycogen and therefore more crude protein per cell dry weight. The wild-type control was grown in Tank E and the mutant was grown in Tank F. The available nitrogen, provided in the form of nitrate, was modulated to either result in a nitrogen unlimited or a nitrogen limited condition, while the amount of methanol ($C_1$ substrate) provided was held constant. This resulted in a nitrogen limited condition relative to the amount of carbon provided by the methanol, which would otherwise enable amino acid biosynthesis and cell growth. For wild-type control cells, the nitrogen limited condition would trigger glycogen accumulation in the presence of abundant carbon. Biomass samples were collected from the fermenters in each condition, centrifuged, lyophilized, and then analyzed by the GCMS assay to measure levulinate as a proxy for glycogen to semi-quantitatively determine the amount of glycogen in each Tank grown under each condition. Table 1 indicates that under the nitrogen-unlimited condition, the wild-type produced two times the measured levulinate in the sample (0.8% vs. 0.4%), whereas under the nitrogen-limited condition, while the levulinate in the mutant strain sample did not increase, that of the wild-type increased nearly 5-fold, to 3.9%. The measured crude protein in the samples indicates that under each condition, the wild-type had slightly or significantly less crude protein than the mutant.

TABLE 1

Biomass composition of WT and G680, ΔglgC, Glycogen (−) on methanol

| Condition | Strain | Levu-linate (μg) | Avg Levu-linate (μg) | % Levu-linate | Total AA (μg) | Avg Total AA (μg) | % AA |
|---|---|---|---|---|---|---|---|
| Unlim. Nitrogen, Methanol | WT | 2.64 2.69 | 2.67 | 0.8 | 109 123 | 116 | 33 |
|  | ΔglgC | 1.28 1.7 | 1.49 | 0.4 | 131 147 | 139 | 40 |
| Limited Nitrogen, Methanol | WT | 14.25 13.02 | 13.64 | 3.9 | 83 73 | 78 | 22 |
|  | ΔglgC | 1.63 1.37 | 1.5 | 0.4 | 130 121 | 125 | 36 |

The AA (amino acids) values indicated in Table 1 are derived from the same GCMS method that is used to assay levulinate. The crude protein was assayed by an external certified lab according to standard protocol. The values differ slightly because not all AA's are detected by the GCMS assay and the crude protein assay result is based upon elemental analysis of nitrogen content in fully combusted samples, which includes all nitrogenous compounds present (e.g., nucleic acids, cell wall components, etc. Cellular nitrogenous components are primarily comprised of amino acids).

Figure 2A:
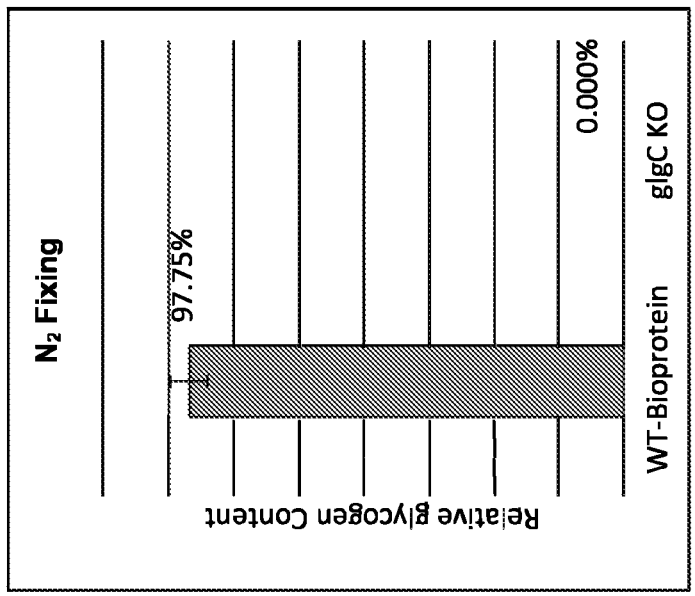

Samples from the same fermentation runs were also assayed enzymatically for glycogen. Cell lysates for the enzymatic glycogen assay were prepared by sonicating cell pellets resuspended in a detergent-based cell lysis solution. The enzymatic assay for glycogen detection utilizes three enzymes: (1) amyloglucosidase, which hydrolyzes the glycogen polymer to D-glucose; (2) glucose oxidase, which oxidizes the D-glucose monomers to form hydrogen peroxide; and (3) horseradish peroxidase, which generates a fluorescent product when hydrogen peroxide reacts with a highly sensitive, stable non-fluorescent substrate. The intensity of fluorescence correlates with the amount of glucose present and therefore the initial amount of glycogen in the sample (Bruss and Black, *Anal. Biochem.* 84:309-12, 1978). FIGS. 2A and 2B show relative glycogen production of the ΔglgC mutant as compared to wild-type, with wild-type glycogen production under the nitrogen unlimited condition set to 100%. As shown in FIGS. 2A and 2B, it was determined that for the ΔglgC mutant, although the mutant biomass contained hexoses that gave rise to levulinate in the hydrolysis assay, no actual glycogen was detected in the nitrogen limited condition (FIG. 2A, "$N_2$ Fixing"), and only a very small amount (0.0019% relative to the control) was detectable in the nitrogen unlimited condition (FIG. 2B, "$NO_3$"). In contrast to the ΔglgC mutant, the wild-type control produced glycogen measurable via this specific enzymatic assay under both nitrogen limited and nitrogen unlimited conditions.

This phenotype therefore provides an opportunity to consistently produce biomass that is enriched in synthesis of a desired product (such as amino acid synthesis), and not the storage polymer glycogen.

Example 3

Growth of Glycogen-Null *M. Capsulatus* Bath with Methane in a Continuous Culture System This example demonstrates the increased crude protein per dry cell weight in glycogen-null mutant methanotrophic bacteria (*M. capsulatus* Bath ΔglgC) as compared to the wild-type under methane fermentation with nutrient limitation condition. In order to evaluate glycogen-null cells grown in 2 L growth format with methane as the carbon and energy source, the wild-type and the MCA1474 deletion mutant (ΔglgC, labeled Gly (-) in FIGS. 3A and 3B) were grown in 2 L continuous fermentation vessels. Nutrients, including all elements required for growth except nitrogen, oxygen and methane, were provided in a nutrient mixture. This mixture was formulated based upon elemental analysis of wild-type biomass under optimal growth conditions. Maximum possible gas to liquid mass transfer for the equipment was established and maintained throughout the experiment. The nutrient mixture was initially provided to the continuous cultures such that if all elements in it were consumed, the potential dry cell weight in the broth would be 15 g/L. However, under maximum mass transfer conditions, the maximum biomass concentration was only 7-8 g/L, resulting in an excess of nutrients. To determine the impact of nutrient limitation on the wild-type and the mutant, this nutrient feed was then decreased to a potential biomass concentration value of 12, 10, 7 g biomass/L of broth while mass transfer of the gases was held constant. Thus, an imbalance between carbon and nutrient availability was achieved in which carbon was abundant but nutrients were limiting. Conditions for the methane fermentation continuous culture are provided in Table 2.

TABLE 2

Parameters for Continuous Culture with Methane

| Parameter | Conditions |
|---|---|
| Nitrogen feed | 0.5M $HNO_3$ |
| Nutrient supply, Nutrient Master Mix (NMM) | Not limiting conditions |
| NMM Power | Supports growth up to 15 g/L of DCW |
| Working volume | 1.5 (L) |
| Micro-sparger (20 uM) | Methane |
| Ring sparger | Air |
| Temperature | 42° C. |
| pH set point | 6.5 |
| pH control | 1N NaOH, 0.5M $H_2SO_4$ |
| Agitation | 1200 (RPM) |
| Aeration, Sartorius MFC | 800 (mL/min) |
| Methane flow, Alicat MFC | 112 (mL/min) |
| Supply Oxygen/Methane Ratio | 1.6 (v/v) |
| Dilution Rate | 0.1 (1/hour) |

Biomass Collection

Throughout the experiment, wash-out periods were applied prior to condition changes, for 20-24 hours or two fermentation volumes. For each set of conditions, two to three liters of the fermentation broth out (FBO) were collected, which is a volume sufficient to obtain 15-20 grams of dry cell weight biomass. After collection, the FBO was centrifuged and the wet cell pellets were stored at −80° C. Gas analysis was performed at various stages of the collection process. Next, pellets were lyophilized, and the dry cell biomass was subjected to crude protein analysis.

Glycogen Detection by GCMS

Biomass samples were collected from the fermenters in each condition, centrifuged, lyophilized, and then analyzed via the GCMS method mentioned above. A GCMS assay that detects levulinate as a proxy for glycogen was used to determine the relative amount of glycogen in each tank grown under each condition. The GCMS determination of glycogen is based upon the detection of levulinic acid (levulinate), which is a keto acid formed from hexoses such as glucose during acidic hydrolysis of biomass. To evaluate the relative glycogen concentration in biomass, cell pellets were digested in 6N HCl for 24 hours at 100° C. followed by neutralization with sodium hydroxide. The resulting hydrolyzed cell biomass was centrifuged. Levulinate derived from hydrolyzed glycogen in the supernatant was derivatized with methyl chloroformate to generate methyl levulinate. Methyl levulinate was extracted with chloroform and analyzed with a GC-MS. Quantification of levulinate was achieved with calibration standards including levulinate derivatized using methyl chloroformate. Linear recovery of glycogen and glucose via acid hydrolysis followed by levulinate analysis with this method was validated with known amounts of standard. (Smart K F, Aggio R B, Van Houtte J R, Villas-Bôas S G. *Nat Protoc.* 2010 September; 5(10): 1709-29). This method to detect glycogen is semi-quantitative (i.e. relative amounts of glycogen may be measured via this method). Since this method represents all hexoses present in the cells, it is not specific for glycogen.

Results

Figure 3B:
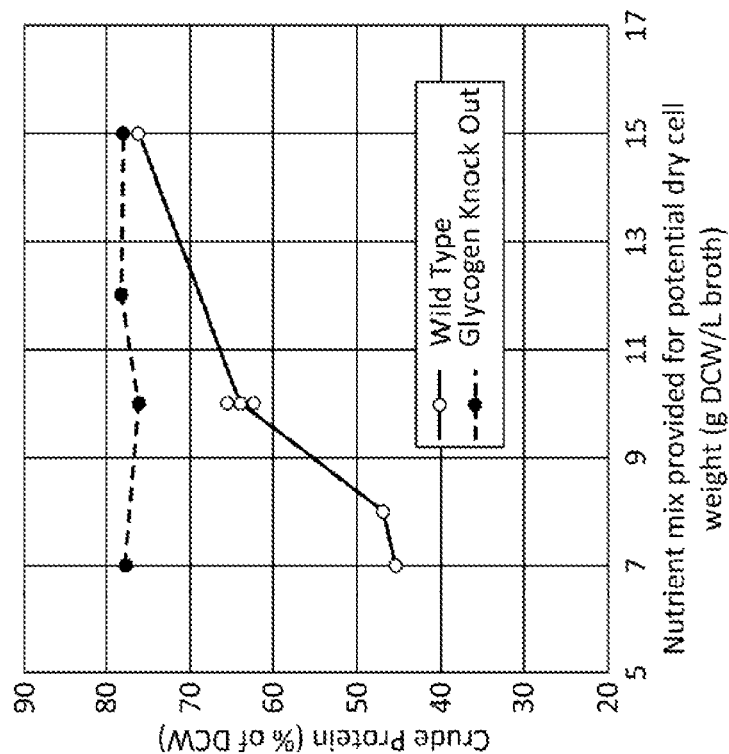
FIGS. 3A and 3B show effects of nutrient limitation on the resulting biomass compositions of the *M. capsulatus* Bath ΔglgC strain grown under methane fermentation in a continuous culture system.
Figure 3A:
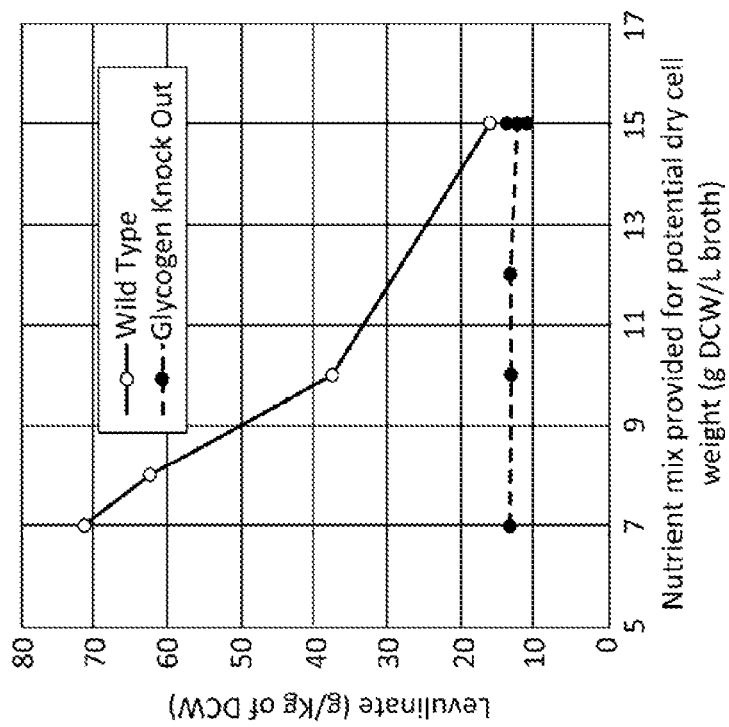

FIGS. 2A and 2B show the effect of the nutrient limitation on the resulting biomass composition. The amount of levulinate in g/kg of dry cell weight (and glycogen) in each strain in each condition is shown in FIG. 3A. As shown in FIG. 3A, as the nutrients became more limiting, glycogen accumulated in the biomass of the wild-type control but not the glycogen-null mutant. Crude protein was assayed and is indicated as a percentage of dry cell weight for each condition and strain in FIG. 3B. As shown in FIG. 3B, as the nutrients became more limiting, the crude protein in the glycogen-null mutant per dry cell weight remained constant just below 80%, whereas the wild-type control decreased down to approximately 45%. The results of the levulinate assay are consistent with the results of the iodine staining the enzymatic assay for glycogen. The levulinate assay can be used for relative quantification of glycogen content (by comparing the mutant levulinate level to the control levulinate level), but does not represent an absolute concentration of glycogen in the biomass because the conversion of glycogen to levulinate is incomplete.

Example 4

Glycogen Production Under Nitrogen Limitation

Figure 4:
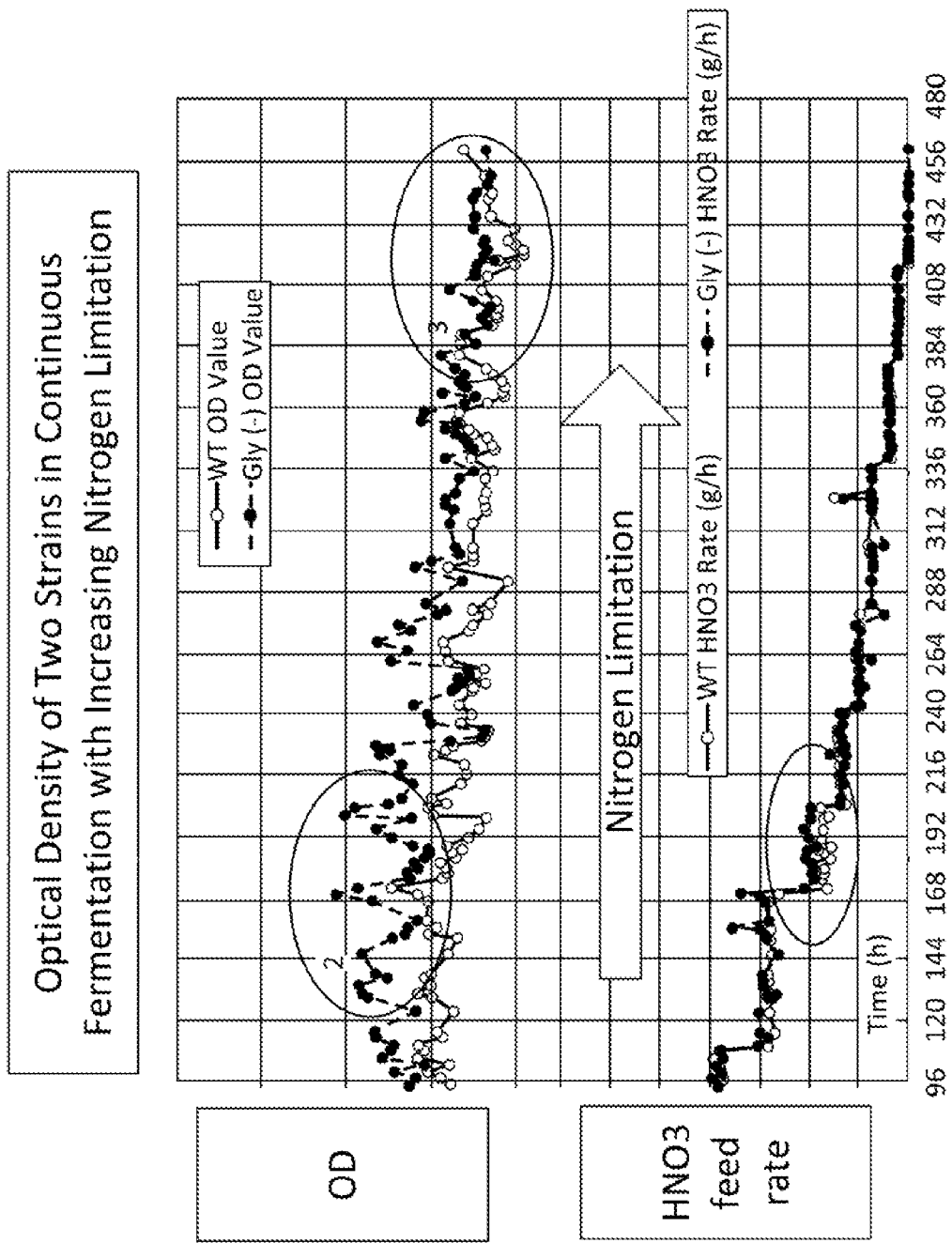
FIG. 4 shows profiles for the glycogen-null ΔglgC strain ("Gly(-)") and the wild-type strain ("WT") during continuous culture with a 0.5 M $HNO_3$ feed rate. Optical density (OD) is shown in the top panel, and the $HNO_3$ feed rate (g/h) is shown in the bottom panel.

The objective of this example was to evaluate the effect of increasing nitrogen limitation on glycogen-null mutant methanotrophic bacteria (*M. capsulatus* Bath ΔglgC). FIG. 4 shows profiles for the glycogen-null ΔglgC strain and the wild-type strain during continuous culture with a 0.5 M HNO$_3$ feed rate. The experiment started with non-limiting nitrogen, and the amount of nitrogen in the form of HNO$_3$ was decreased over time to create nitrogen limiting conditions. The optical density at 600 nm (OD$_{600}$) was measured throughout the experiment to determine the dry cell weight (top panel). With a minor exception (circled on the bottom graph), the HNO$_3$ delivered to the cultures was equivalent, but the glycogen null strain consistently had a higher OD (see, for example, the two circled sections of the top panel).

Figures 5A, 5B:
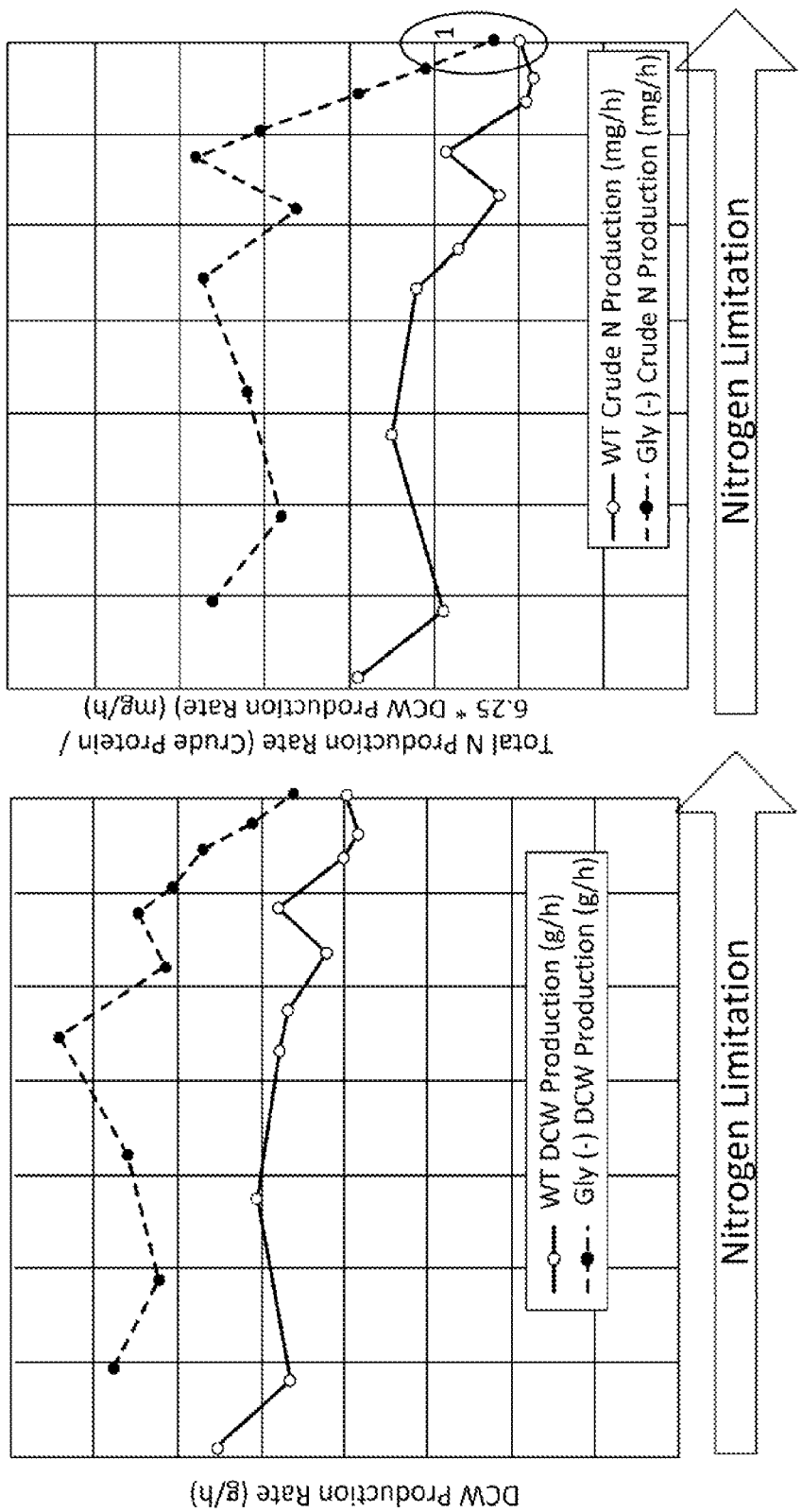
FIGS. 5A and 5B show effects of increasing nitrogen limitation for wild-type *M. capsulatus* Bath versus the *M. capsulatus* Bath ΔglgC strain.

FIG. 5A shows the dry cell weight (DCW) of the culture under different nitrogen limitation conditions. Dried material from each condition was assayed for crude protein analysis by a certified lab according to standard protocol and these values were used to determine total nitrogen production, which is represented in FIG. 5B. At each condition, the glycogen-null strain had higher crude nitrogen production per DCW compared to the wild-type strain.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/785,668, filed on Dec. 27, 2018, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A modified *Methylococcus capsulatus*, comprising:
   (i) a chromosomal knock-out of a glgA2 isoform of a glycogen synthase gene, or
   (ii) a chromosomal knock-out of an ADP-glucose pyrophosphorylase gene and a chromosomal knock-out of a glgA2 isoform of a glycogen synthase gene, wherein the modified *Methylococcus capsulatus* cultured under conditions comprising a non-limiting amount of a $C_1$ substrate produces:
   at least about 30% less glycogen as compared to the parent *Methylococcus capsulatus* cultured under the same conditions; and/or
   at least about 5% more crude protein as compared to the parent *Methylococcus capsulatus* cultured under the same conditions.

2. The modified *Methylococcus capsulatus* of claim 1, wherein the *Methylococcus capsulatus* is *Methylococcus capsulatus* Bath.

3. The modified *Methylococcus capsulatus* of claim 1 or claim 2, wherein the culture conditions further comprise the presence of a limiting amount of a nutrient or metabolite required for growth.

4. The modified *Methylococcus capsulatus* of claim 3, wherein the limiting amount of the nutrient required for growth comprises a limiting amount of nitrogen.

5. The modified *Methylococcus capsulatus* of claim 1, wherein the production of at least about 5% more crude protein as compared to the parent *Methylococcus capsulatus* further comprises a culture condition comprising from about 20% to about 80% nitrogen fixation.

6. The modified *Methylococcus capsulatus* of claim 1, wherein the modified *Methylococcus capsulatus* has a lower ratio of utilized oxygen to utilized methane as compared to the parent *Methylococcus capsulatus*.

7. The modified *Methylococcus capsulatus* of claim 1, wherein the chromosomal knock-out of the ADP-glucose pyrophosphorylase gene comprises an inactivating deletion comprising the polynucleotide sequence of SEQ ID NO:1.

8. The modified *Methylococcus capsulatus* of claim 1, wherein the chromosomal knock-out of the glgA2 isoform of the glycogen synthase gene comprises an inactivating deletion comprising the polynucleotide sequence of SEQ ID NO:3.

9. The modified *Methylococcus capsulatus* of claim 1, wherein the chromosomal knock-out comprises a knock-out of the ADP-glucose pyrophosphorylase gene and a knock-out of the glgA2 isoform of the glycogen synthase gene.

10. The modified *Methylococcus capsulatus* of claim 1, wherein the modified *Methylococcus capsulatus* further comprises a chromosomal knock-out of a phosphoglucomutase gene and/or a glycogen branching enzyme gene.

11. The modified *Methylococcus capsulatus* of claim 10, wherein the knock-out of the phosphoglucomutase gene is a knock-out of SEQ ID NO:4 or 5.

12. The modified *Methylococcus capsulatus* of claim 10, wherein the knock-out of the glycogen branching enzyme gene is a knock-out of SEQ ID NO:6.

13. The modified *Methylococcus capsulatus* of claim 1, wherein the modified *Methylococcus capsulatus* further comprises increased expression of an endogenous glycogen catabolism enzyme.

14. The modified *Methylococcus capsulatus* of claim 13, wherein the glycogen catabolism enzyme is a glycogen phosphorylase, a glycogen debranching enzyme, an adenosine diphosphate sugar pyrophosphatase, or any combination thereof.

15. The modified *Methylococcus capsulatus* of claim 13, wherein the increased expression of the endogenous glycogen catabolism enzyme is increased expression of SEQ ID NO:10, SEQ ID NO:11, SEQ ID NO:12, SEQ ID NO:13, or any combination thereof.

16. The modified *Methylococcus capsulatus* of claim 1, wherein the modified *Methylococcus capsulatus* further comprises a heterologous nucleic acid encoding a glycogen catabolism enzyme.

17. The modified *Methylococcus capsulatus* of claim 16, wherein the glycogen catabolism enzyme is a glycogen phosphorylase gene, a glycogen debranching enzyme gene, an adenosine diphosphate sugar pyrophosphatase gene, or any combination thereof.

18. The modified *Methylococcus capsulatus* of claim 1, wherein the modified *Methylococcus capsulatus* further comprises a heterologous nucleic acid encoding a glycolysis pathway enzyme.

19. The modified *Methylococcus capsulatus* of claim 1, wherein the modified *Methylococcus capsulatus* further comprises a heterologous nucleic acid encoding a biosynthesis enzyme to produce a desired product.

20. The modified *Methylococcus capsulatus* of claim 19, wherein the encoded biosynthesis enzyme is an amino acid biosynthesis enzyme selected from the group consisting of a lysine biosynthesis enzyme, a tryptophan biosynthesis enzyme, a methionine biosynthesis enzyme, a cysteine biosynthesis enzyme, and a threonine biosynthesis enzyme.

21. The modified *Methylococcus capsulatus* of claim 20, wherein the encoded biosynthesis enzyme is a lysine biosynthesis enzyme selected from the group consisting of a lysine-sensitive aspartokinase III, an aspartate kinase, an aspartate-semialdehyde dehydrogenase, a dihydrodipicolinate synthase, a dihydrodipicolinate reductase, a 2,3,4,5-tetrahydropyridine-2,6-carboxylate N-succinyltransferase, an acetylornithine/succinyldiaminopimelateaminotransferase, a succinyl-diaminopimelate desuccinylase, a succinyl-diaminopimelate transaminase, a diaminopimelate epimerase, a diaminopimelate dicarboxylase, or any combination thereof.

22. The modified *Methylococcus capsulatus* of claim 21, wherein the *Methylococcus capsulatus* expresses a deregulated endogenous aspartokinase activity.

23. The modified *Methylococcus capsulatus* of claim 22, wherein the deregulated endogenous aspartokinase activity is an aspartokinase mutant that is resistant to feedback inhibition by one or more of lysine, threonine, and methionine.

24. The modified *Methylococcus capsulatus* of claim 22, wherein the deregulated endogenous aspartokinase activity is encoded by a mutant thrA gene, metL gene, lysC gene or any combination thereof, each comprising a spontaneous mutation, random mutation, site specific mutation, or any combination thereof.

25. The modified *Methylococcus capsulatus* of claim 19, wherein the heterologous nucleic acid encoding the biosynthesis enzyme further comprises a heterologous control element that activates or increases expression of one or more biosynthesis enzymes as compared to the biosynthesis enzyme comprising its native control element.

26. The modified *Methylococcus capsulatus* of claim 25, wherein the heterologous control element comprises a modified, endogenous promoter that regulates dihydrodipicolinate synthase, wherein the modification to the endogenous promoter increases lysine production.

27. The modified *Methylococcus capsulatus* of claim 20, wherein the encoded biosynthesis enzyme is a tryptophan biosynthesis enzyme selected from the group consisting of a chorismate-pyruvate lyase, an anthranilate synthase component I, an anthranilate synthase component II, an anthranilate phosphoribosyltransferase, a phosphoribosylanthranilate isomerase, a tryptophan biosynthesis protein, an N-(5'phosphoribosyl) anthranilate isomerase, an indole-3-glycerol phosphate synthase, a tryptophan synthase alpha chain, a tryptophan synthase beta chain, and any combination thereof.

28. The modified *Methylococcus capsulatus* of claim 20, wherein the encoded biosynthesis enzyme is a methionine methionine biosynthesis enzyme selected from the group consisting of a homoserine O-acetyltransferase, a homoserine O-succinyltransferase, a cystathionine gamma-synthase, a protein MalY, a cystathionine beta-lyase, a B12-dependent methionine synthase, a 5-methyltetrahydropteroyltriglutamate-homocysteine S-methyltransferase, O-acetylhomoserine aminocarboxypropyltransferase, or any combination thereof.

29. The modified *Methylococcus capsulatus* of claim 20, wherein the encoded biosynthesis enzyme is a cysteine biosynthesis enzyme selected from the group consisting of a serine acetyltransferase, a cysteine synthase A, a cysteine synthase B, and any combination thereof.

30. The modified *Methylococcus capsulatus* of claim 20, wherein the encoded biosynthesis enzyme is a threonine biosynthesis enzyme selected from the group consisting of an aspartate transaminase, a PLP-dependent aminotransferase, an aspartate aminotransferase, an aspartate kinase, an aspartate-semialdehyde dehydrogenase, a homoserine dehydrogenase, a homoserine kinase, a threonine synthase, and any combination thereof.

31. A method of producing a desired product, the method comprising culturing the modified *Methylococcus capsulatus* of claim 19 under conditions comprising a non-limiting amount of a $C_1$ substrate and for a time sufficient to produce the desired product, wherein the quantity of the desired product is greater than a quantity of the desired product produced by the parental *Methylococcus capsulatus* cultured under the same conditions.

32. The method of claim 31, wherein the culture conditions further comprise the presence of a limiting amount of a nutrient or metabolite required for growth.

33. The method of claim 32, wherein the limiting amount of the nutrient required for growth comprises a limiting amount of nitrogen, sulfur, phosphorous, and/or oxygen.

* * * * *

UNITED STATES PATENT AND TRADEMARK OFFICE
CERTIFICATE OF CORRECTION

| | | |
|---|---|---|
| PATENT NO. | : 12,234,445 B2 | Page 1 of 1 |
| APPLICATION NO. | : 17/293832 | |
| DATED | : February 25, 2025 | |
| INVENTOR(S) | : Renee M. Saville et al. | |

It is certified that error appears in the above-identified patent and that said Letters Patent is hereby corrected as shown below:

In the Claims

Column 49, Claim 3, Lines 32-33:
"of claim 1 or claim 2, wherein" should read: --of claim 1, wherein--.

Column 50, Claim 21, Line 63:
"dicarboxylase, or any combination" should read: --dicarboxylase, and any combination--.

Column 51, Claim 28, Lines 35-36:
"is a methionine methionine biosynthesis" should read: --is a methionine biosynthesis--.

Column 52, Claim 28, Line 6:
"aminocarboxypropyltransferase, or any combination" should read:
--aminocarboxypropyltransferase, and any combination--.

Signed and Sealed this
Sixth Day of May, 2025

Coke Morgan Stewart
*Acting Director of the United States Patent and Trademark Office*

SEQUENCE LISTING

```
<160> NUMBER OF SEQ ID NOS: 13

<210> SEQ ID NO 1
<211> LENGTH: 1275
<212> TYPE: DNA
<213> ORGANISM: Methylococcus capsulatus

<400> SEQUENCE: 1
atgcccgagt cgatgcacgc ctcatcccgt ttcgtaagtc ggctgacccg gcaaaccctg      60
gccctcatcc tggcgggcgg gcgcggaagt cggctgcaga agctcacgga atggcgcgcc     120
aagcctgctg tcccgttcgg cggcaaattc cggatcatcg acttcccgct gtccaactgc     180
gtcaattccg gaatccgcca ggtcggcgtg ctgacccagt acaaggcgga ctcactgatc     240
cgccacattc agcagggctg gggcttcctg cgcggagagc tcggcgagtt catcgacatc     300
atgcctgccc agcagcgtct gcaggaaagc tggtacgcag gcacggcgga tgcggtgtat     360
cagaacttgg acatcatccg ccagcgggac cccgagttca tcatgatcct ggccggtgac     420
cacgtgtaca agatggacta cggcctgatg ctggcctatc acgtggaaag gaaggccgat     480
ctcaccatcg gctgcatgga agtgccgctt gccgatgcga aggcattcgg tgtcatgcag     540
atggacggcg agcagcgtat ccgaaaattc gtcgagaagc cctccgatcc gccgcccatg     600
ccgaaccgcc ccgatcacgc cgccgcatcc atggggatct acatattcaa cacggctttc     660
ctgttcgagc agctcatcaa ggatgccgac accccggct cgaaccacga tttcggcatg     720
gacatcatcc cccaggtcat tcagaaatac cgcgtcttcg cctatcgctt ccgcaacgcc     780
cagagcggcg tgcaggccta ctggcgcgat gtaggcacgg tggactcata ctgggccgcc     840
aacatggagc tgatcggggt cgatccggaa ctgaatttgt acgaccagga atggccgatc     900
```

| | |
|---|---|
| tggacctatc aggctcagac cccgccggcc aagtttgtgt tcgacgatga cgaccggcgc | 960 |
| ggcatggcgg tggactccat ggtttcgggc ggctgcatca tttccggcgc cgaagtccgc | 1020 |
| cactcgttgc tgttttcgaa tgtacgggtg aactcgtttt cacgcgtgct ggattcggtg | 1080 |
| atcctccccg acgtgaacat cgggcgccat tgcaggatca gccgggcggt gatcgacaag | 1140 |
| ggttgcaata ttccgcccaa taccgtcatc ggcgaaaacc tcgaggatga ccgcaaacgg | 1200 |
| ttttacgtca gccccgaggg catcgttctg gtgacccccg attgtctcgg ccagaggctg | 1260 |
| catttccacc gctga | 1275 |

<210> SEQ ID NO 2
<211> LENGTH: 1482
<212> TYPE: DNA
<213> ORGANISM: Methylococcus capsulatus

<400> SEQUENCE: 2

| | |
|---|---|
| atgaagatcc tgttcgtctc cagtgaggtc ttcccccctga tgaagaccgg cggactcgcg | 60 |
| gacgtctccg gcagcctgcc ggcggccttg tccgccctgg gtcatgatgt gcgtatcctg | 120 |
| atgccggcat acccggaagc catctccgcc gccgaaaccc caacgcgct gagtctgcgt | 180 |
| caggcgggca gtcagctgac cctgctgtcg acgcgcttgc cgggcaccac cgtgcccctc | 240 |
| tggctgctgg acgcaccggc ttcgttcggc cgcttcggca accttacct ggcacccaac | 300 |
| ggtgccccct ggcccgacaa tgccgaacgt ttcgctctgc tcgcgcgtgt cgccgtcgac | 360 |
| ctcacccagg accggctcgg cctcggctgg aaacccgatg tcgtccattg caatgactgg | 420 |
| caaaccggtt tgatcccgcc gcttttgagc gacgagccga tcgtccggc cgtggtgttc | 480 |
| accgtccaca atctcgccta ccaaggtctg ttcccctacg aaacctttca acgcctggcg | 540 |
| ctccctcccc gtctctggaa gatggaggca ctggagttct acggcagct tccttcatc | 600 |
| aagggagggt tggtattcgc cgaccgcatc aacacggtga gtccaagcta tgccgaagag | 660 |
| atccagaccc cggagttcgg ctgcggcctg gacggtctgc tcagaagccg caagtcatgc | 720 |
| ctgagcggga ttctcaacgg tatcgacgac gtggcctgga atccggccac cgatccctat | 780 |
| cttcccgcgc cctacggccc ggatacctg gagcggaaaa aggtcaaccg cacggtgctc | 840 |
| agacagcggt acggcctgcc ggacgacccg gaggtcgccg tgctcggaat ggtgggaagg | 900 |
| atggtcgagc agaagggagt ggacctgttg atcgacattc tggatgatct gctgcagttg | 960 |
| ccggtccagc tcgtcgtcct gggcagcggc gacaaggaat cgaacgctg cttcgaaagg | 1020 |
| gccgccgcag cccgtccgga cgtatcgcc gtcaccatcg gctatgacga accgctggcc | 1080 |
| catctcatcg aagccggcgc cgatatcttt ctgatgcctt cccgcttcga gccctgcggc | 1140 |
| ctgaaccaac tctatagtca gcgctaccgg accgtaccga tcgtgcgcaa ggtcggcgga | 1200 |
| ctcgcggaca ccgtggaaga tgccacgccc gagcgccttg cggccggaca ggccagcggc | 1260 |
| atcgtgttcg agccggccaa gcccgccttc tgctggagg ccgtctaccg cgccctggcg | 1320 |
| ctgtaccggg agcccgaggt ctggcgggcg gtctgcaagt gcggcatggc caaggatttt | 1380 |
| tcctggcgca agagtgcctc ccggtatgtc ggactctacc gggaggcact ggccggaatg | 1440 |
| aatgccggct gctccatcgc cgaccccgc tgtgcggcct ag | 1482 |

<210> SEQ ID NO 3
<211> LENGTH: 1542
<212> TYPE: DNA
<213> ORGANISM: Methylococcus capsulatus

<400> SEQUENCE: 3

```
atgccggaaa gccgggccga ggttgcgccg gagccgtcgc ccccgcctca catccagcac      60
cggcccgccc tgttcgtggt ccatgtcacg ccggaactgg cgccggtggc gaaggtcggc     120
gggctggcgg atgtggtgtt cggactcggg cgggagctgg agatccgcgg caatcacgtc     180
gaaatcattt tgcccaagta cgactgcatg cgctacgacc aaatctgggg tctgcagcgc     240
accttcgatg acctgtgggt gccctggtat ggtggagcca tccactgctc tgtctatttc     300
ggcttcgtcc acgggcgcaa gtgcttttc atcgagccgc actcccagga caatttcttc     360
aaccgcggtg cggtgtacgg cttccatgac gacattttcc gtttcgcgtt cttttcgcgg     420
gcggcgatgg agttcctctg gaaggccggc aagaatcccg acatcattca ttgccatgat     480
tggcagacgg cactggtgcc ggtctatctg tacgaaatct atcagccgat ggggatgagg     540
catccccggg tctgcttcac catccacaat ttcaagcatc agggcgtcac cggggcgcag     600
gtgctgcacg cctccggact cgaccggccg aatactatt ccactatga ccgtcttcgc      660
gacaaccata atccccatgc catcaatctg atgaagggcg catcgtcta tgccaatttc      720
gtgaccacgg tttcgccgcg ctatgcgatg gaggccaagg atcagggcca gggcttcgga     780
ctcgagccga ccctgcacat ccatcacatg aagtacggcg gggtggtgaa tggcatcgac     840
tacgacgtct ggaatccgga gatcgacccg cacatccccg tgcacttcaa cgtggacacg     900
atcgaaggca aatatgccga caagaaggcg ctgcgcgacc ggctgctgct cgccgacaac     960
gagaaaccca tcgtgtcctt cgtcggccgg ctcgatccgc agaagggcat cgagctgatc    1020
cgccatgcct tgttctatac gttagggcaa ggcggccagt tcgtcctgct cggctccagt    1080
cccgacgggg cgatcaacgg ctatttctgg ggcctgaagc ggcagttcaa cgacaatccg    1140
gactgtcacc tggaaatcgg ctacaacgaa gagctggcgc atctggtcta tgccggctcg    1200
gacgtgatgg tggtgcccag tcgctttgag ccctgcggac tgacccagct gatcgccatg    1260
cgctatggca ccattccggt ggtgcgcgaa atcggcggtc tggcggatac cgtgatcgac    1320
aaggatttct cgcaccgccc gttgcatgag cgcaacggtt acgtattccg cgattacgat    1380
gagcgcggac tggaatcggc gctgggccgg gcgatcgcct gctactatca gtatccggac    1440
cacttccgcg agctgatgaa gaatgccatg cgctacgact attcctggaa ccatccgggg    1500
caggactatc tcaacattta ccactatatc cgggacaaat ag                        1542
```

<210> SEQ ID NO 4
<211> LENGTH: 1635
<212> TYPE: DNA
<213> ORGANISM: Methylococcus capsulatus

<400> SEQUENCE: 4

```
atggcagtgg aaatccgcaa acgacgccc tatccggacc agaaaccggg cacctcgggc       60
ctacgcaaga aggtgaaggt ttttctccag gggaactatc tcgaaaattt cgtccagtcg     120
gtattcgata ccgttgaaac ggcagacggc gccaccctgg tggtgggggg cgatggccgc     180
tatttcaacc gccaggcgat ccagatcatc ctgcgcatgg cggccgccaa tggcgtgggg     240
cgggtgctgg tggggcgggg gggcttgctg tcgacaccgg cggcctcctg cgtaatccgt     300
aaacacaggg cactgggcgg tttcgtgctg tcggccagtc acaatcccgg cggtccggag     360
gaagacttcg gcatcaagtt caacgtcgcc aacggcggtc ccgccccgga gagtttcacc     420
gaccgggtgt accagcgcag ccgggtcatc gacgcctacc gcatcgtgtc cgctcctgat     480
ctggacatcg acaccccggg ccgctcccgc atcggtgaca tggagatcga agtcattgat     540
```

```
ccggtggccg attatgccga gctgatggag cacctgttcg atttcgggtt gatccgctcg      600
ggtttccgct ccggcgcgct gaccctgcgc ttcgatgcga tgcatgcggt caccggccct      660
tatgcgaagc gcatcctcga agagacgctc agcgcggcgc ccggatcggt ggtcaacgcc      720
gtgccgctgg aggatttcgg cggcggccat cccgatccga acctggtgca cgcccgtgag      780
ctggcggcgg tgatgtacag cggccggccg ccgaccctgg gggctgcctc cgacggtgac      840
ggcgaccgca acatgatcat gggtgccaac tgtttcgtca cgcccagtga cagcctggcg      900
atcctcgcag ccaacgccca tctggtgccg ggttacaagg atggcttgcg cggcgtggcc      960
cggtccatgc ccaccggccg cgcggtcgac agggtggcgg cggcgatggg gatcgagtgc     1020
tacgagacgc cgaccggctg gaagttttc ggcaatctgc tcgatgcccg caggatcacg      1080
ttgtgcggcg aggagagttt cggcaccggc tccgaccacg tccgggaaaa ggacggcctg     1140
tgggccgtgt tgttctggct gaatctgatc gccctgcgca agcagtcggt ggccgccatc     1200
gtggccgacc actggcgccg gttcgggcgt gattattatt cgcggcacga ttatgaaggc     1260
atcgaggtgc ccgtagccga ggggatcatg gggcgtctgc aggatctgct ggccgagctt     1320 cccgccgcg ccttcggtga ctaccgggtg acgctggccg acgacttccg ctacgtcgac      1380
ccggtcgacg gcagcgtcag cgagcaccag ggtatccgga tcgccttcga caattcgtcc     1440
cgtatcgtgt tccgcctctc ggggaccggc accgagggcg ccaccctgcg cgtttacatg     1500
gagcgctacg agcgtgatcc gaacctgcac aatctgccga cccaggaggc gctggcggac     1560
ttgatcgcga tcgccgagga tctgtgccag gtcaaaaagc gcacgggcat ggcccagccc     1620
agcgtcatga cctga                                                     1635

<210> SEQ ID NO 5
<211> LENGTH: 1392
<212> TYPE: DNA
<213> ORGANISM: Methylococcus capsulatus

<400> SEQUENCE: 5
atggaaattg agccgattcc atccatcgcc cccaccctgt tccgggccta cgacattcgc       60
ggcatcgtcg gcgacacctt gacggaggct gcggcccgag cgatcggccg ggccgtcggc      120
agcgaagcgc tcgaccgcgg cgaacggcag gtcgtcgttg cccgcgacgg gcggctgagc      180
agccccgcgc ttggcgccgc gctggcggag gggctgcgga tggccggctg ccaggtcacc      240
gatctggggc tggcgcccac gccggttctc tatttcggca cccatgtgct ggcggggcgt      300
tccggcgtga tggtgaccgg cagccacaat cccgcgaatt acaatggctt caagatcgtg      360
ctggcaggac agacgctggc cggcgaggat attcagagac tgaggcagcg tatcgaaacg      420
ggggacttcc ggaccgggga gggggagatc gagcgtcggg atctgctgtc cgattaccaa      480
cggcgtatcg tggacgacgt acagctcggc cggccgttca agtcgtggt cgattgcggc      540 aacggcgtgg cggcggtggt ggcgccacag gtcctccggg ccatggattg cgaagtggtc      600
gaattgttct gcaccgtcga cggcaatttc ccccatcatc atcccgatcc gagcaagccg      660
gagaacctgg cggcgctgat cgaaacggtc aagcgggaag gcgcggatct gggcgtggcc      720
ttcgacggcg atggcgaccg gctcggcgtg gtcgactcgg ccggcaacgt catctggccg      780
gatcggcaga tgatgctgtt cgccgccgac gtgctgtccc gcgagccggg cgcggacatc      840
atctacgacg tcaaatgcac ccgtcatctg gcgggctaca ttctgcgtca cggggccgc      900 ccgctgatgt ggaagaccgg ccattccctg atcaaggcca agatgaagga aaccggcgct      960
```

```
ctgctggcgg gggagatgag cggccacttc ttcttcaggg agcgctggta cggtttcgac    1020
gacggcatct acgcctgcgc ccggatggtg gaaatcctgt ctgccgattc tcgcgccacc    1080
gcggaagtgt tcgcggaact gccggacagc gtcaacacgc tgaactcgg tgtgcggttg     1140 caggagggcg aaaacctcgc cttcgtcgaa agaatgcgtg ccctggccga tttcgatgat    1200
ggtcgcatca cggacatcga cggcctgcgg gtcgatttcg ccgacggttg ggggctggta    1260
cgcgcctcca ataccacgcc ttccctggtg atccgcttcg aagccgatac cgccgaaggg    1320
ctggcccgca tccagcagcg cttccgggcg cttctgctga aggtgcggcc cggtctcgag    1380 ctgccttct ag                                                         1392
```

<210> SEQ ID NO 6
<211> LENGTH: 2223
<212> TYPE: DNA
<213> ORGANISM: Methylococcus capsulatus

<400> SEQUENCE: 6

```
ttgacggaca gctcgacctt ggcagaactc tcgccggact tccagcgcat cgttgaagcc     60
cgccatcacg atccgtttgc ggtactgggc cgccaccggc gggacaaccg ggatctcatc    120
cgcgcttttc tgcctcaagc cgaagaagtg cgggtcggat ccgccggacg cgtcatggag    180
cgcatcgctg gtaccgccat tttcgaatgc gaggtcgagg cggaaaccac cgatctgcac    240
tacaggttgt attggaccga ccagacggga cagacccaca gctttatcga tccatacacc    300
ttccctcccc ggctatccga cttcgatctc tatctcttcg gagaagggcg gcactggaac    360
atctaccgcg ttctgggcgc ccatccccac agcgtcgacg tatcgacgg catcctgttc      420 gcgacctggg cccctaacgc cgaacgcatc agcgtagtcg agaattcaa tggctgggat    480 ggtcgccggc accccatgcg ggtgcgtggc gccagcggcg tgtgggaatt gttcattccg    540
gaactgcagc cggggctgct gtacaagttc gagatacgca accgggcgca tggaaccatc    600
catctcaaga gcgacccta cggggcgcag ttcgaacttc ggccgaacac cgcctcgatc      660
atcacccgcg agagcggcta tgcctggaat gatgccgact ggctcgcaca gcgcaaggat    720
tggccctggt tgcaccggcc actgtcggta tacgagatgc atgccggttc ctggaagcgt    780
gatctcgagg gcggatatct gaactatcgc gatctcgccc acgaactggt cgactacgtc    840
aagtcggcgg gcttcagcca catcgagctg atgccggtga cggaacatcc gctggacgcc    900
tcctggggct accagaccac cggctatttc gctcccacca gccgcttcgg cacgcccgac    960
gatttccgtt atttcgtcga tcattgccat cggaatggca tcggcgtgat cctggactgg   1020
gtcccggcgc atttttcccaa ggacgcccat ggtctggccc gcttcgacgg cacggcactg   1080
tacgagcacg aagatcctcg cttgggcgag caccgcgatt gggcacgct gatctataac     1140 tatggccgca acgaggtcaa gaatttcctg ctgggcagcg cgctgttctg gctggaggaa   1200
ttccatctcg acggcctgcg cgtcgatgcc gtcgcctcga tgctctatct cgattattcg    1260
cgccagccgg gcgactggat acccaacaag tacggtggca acgagaatct ggaggccatc   1320
gccttccttc gcgatctcaa taccgtcgtg caccagcagt ttccccggcgt cctggtcatc   1380 gccgaggaat cgaccgcctg gccccaggtc accggccga cttggaccgg gggactgggc    1440
ttctccatga agtggaacat gggctggatg cacgacatcc tggtctatat gggcaaggat   1500
ccggtgcacc ggcattacca tcacgaccag ctcaccttcg gcctgctgta tgccttcacc    1560
gaaaacttcg tcctgccctt ctcgcacgat gaagtcgtcc atggcaaggg ttccatgctg    1620
gcgaagatgc cgggcgacga atggcggcgc ttcgccaacc tgcgtgtcct atacaccatg    1680
```

```
atgttcacct accccggcaa gaagctgctg ttcatgggct gtgaattcgc ccagaccggt    1740
gaatggaacc acacgacggc gctggactgg ccgctgctcg aatccaacct gcacaagggg    1800
gtgctgcatc tggtgagcga cctgaaccgc ctgtaccaaa gcacctccgc gctctatgcc    1860
tacgatttcg aaagccaggg cttcgagtgg atagacagcc acgatgcggc gcagtcagtc    1920
atcagctatg tccgccggga tgatgacagc cacgtcgtcg tggtcttgaa cttcaccccg    1980
gtaccgcgcc acaactaccg cattggcgtg ccggagccgg ttggctaccg tgaggtgttc    2040
aattccgacg ccgaatgcta tggcggcgcc aatctcggca actgggaaat caagaccgag    2100
agcgtggaat ggatgggacg cgcccagtcc gtcgtgctga cccttccgcc cctggccggc    2160
atcgtgcttg cacccgtcgc accgtccgcc actcctgact gcggaacgcc gggcgacgaa    2220
tga                                                                  2223
```

<210> SEQ ID NO 7
<211> LENGTH: 1431
<212> TYPE: DNA
<213> ORGANISM: Artificial Sequence
<220> FEATURE:
<223> OTHER INFORMATION: in-frame deletion in glgC locus

<400> SEQUENCE: 7

```
caaccagggc caatccttgc gctgtgcgag ccagtcggca tcattccagg catagccgct      60
ctcgcgggtg atgatcgagg cggtgttcgg ccgaagttcg aactggcgcc cgtaggggtc     120
gctcttgaga tggatggttc catgcgcccg gttgcgtatc tcgaacttgt acagcagccc     180
cggctgcagt tccggaatga acaattccca cacgccgctg gcgccacgca cccgcatggg     240
gtgccggcga ccatcccagc cattgaattc tccgactacg ctgatgcgtt cggcgttagg     300
ggcccaggtc gcgaacagga tgccgtcgat accgtcgacg ctgtggggat gggcgcccag     360
aacgcggtag atgttccagt gccgcccttc tccgaagaga tagagatcga agtcggatag     420
ccggggaggg aaggtgtatg gatcgataaa gctgtgggtc tgtcccgtct ggtcggtcca     480
atacaacctg tagtgcagat cggtggtttc cgcctcgacc tcgcattcga aaatggcggt     540
accagcgatg cgctccatga cgcgtccggc ggatccgacc cgcacttctt cggcttgagg     600
caggaaagcg cggatgagat cccggttgtc ccgccggtgg cggcccagta ccgcaaacgg     660
atcgtgatgg cgggcttcaa cgatgcgctg gaagtccggc gagagttctg ccaaggtcga     720
gctgtccgtc aaaccgcatc cctcccggtc ggattcactt tgctggattt ctgatagtac     780
aatgccggca cgccggtgcc ggaatatgcg atatctgcgg caggatgtta ccagatttcc     840
caccgcgttt gccccagcca ggaacaggaa tcaggagtcc cctaactcgt tttcacgcgt     900
gctggattcg gtgatcctcc ccgacgtgaa catcggcgc cattgcagga tcagccgggc     960
ggtgatcgac aagggttgca atattccgcc caataccgtc atcggcgaaa acctcgagga    1020
tgaccgcaaa cggttttacg tcagcccga gggcatcgtt ctggtgaccc ccgattgtct    1080
cggccagagg ctgcatttcc accgctgatt gcgattcgga aggtgcaggc cggagggtcc    1140
ggaccgccgc tccacccgtt gttttcggtg tcacagcccc atggatgctc acggaatttt    1200
cgaccggcgc gcgcgggta ttctgctcca catcagttcc ctgccggcg gaccgggaaa    1260 cggcgatctg ggggccgaat ccttccgttt cgtggatttc ctcgctgcgg cgggtgtttc    1320
ggtatggcag acactgccca tcaatcccac ccacgaggac ggttcacctt atcagtgtac    1380
atccgtgcac gccggcaatc cgctcttgat cgggttggac tggttgattg c              1431
```

<210> SEQ ID NO 8
<211> LENGTH: 2481
<212> TYPE: DNA
<213> ORGANISM: Methylococcus capsulatus

<400> SEQUENCE: 8

| | | | | | | |
|---|---|---|---|---|---|---|
| caaccagggc | caatccttgc | gctgtgcgag | ccagtcggca | tcattccagg | catagccgct | 60 |
| ctcgcgggtg | atgatcgagg | cggtgttcgg | ccgaagttcg | aactggcgcc | cgtaggggtc | 120 |
| gctcttgaga | tggatggttc | catgcgcccg | gttgcgtatc | tcgaacttgt | acagcagccc | 180 |
| cggctgcagt | tccggaatga | acaattccca | cacgccgctg | cgccacgca | cccgcatggg | 240 |
| gtgccggcga | ccatcccagc | cattgaattc | tccgactacg | ctgatgcgtt | cggcgttagg | 300 |
| ggcccaggtc | gcgaacagga | tgccgtcgat | accgtcgacg | ctgtggggat | gggcgcccag | 360 |
| aacgcggtag | atgttccagt | gccgcccttc | tccgaagaga | tagagatcga | agtcggatag | 420 |
| ccggggaggg | aaggtgtatg | gatcgataaa | gctgtgggtc | tgtcccgtct | ggtcggtcca | 480 |
| atacaacctg | tagtgcagat | cggtggtttc | cgcctcgacc | tcgcattcga | aaatggcggt | 540 |
| accagcgatg | cgctccatga | cgcgtccggc | ggatccgacc | cgcacttctt | cggcttgagg | 600 |
| caggaaagcg | cggatgagat | cccggttgtc | cgccggtgg | cggcccagta | ccgcaaacgg | 660 |
| atcgtgatgg | cgggcttcaa | cgatgcgctg | gaagtccggc | gagagttctg | ccaaggtcga | 720 |
| gctgtccgtc | aaaccgcatc | cctcccggtc | ggattcactt | tgctggattt | ctgatagtac | 780 |
| aatgccggca | cgccggtgcc | ggaatatgcg | atatctgcgg | caggatgtta | ccagatttcc | 840 |
| caccgcgttt | gccccagcca | ggaacaggaa | tcaggagtcc | cctatgcccg | agtcgatgca | 900 |
| cgcctcatcc | cgtttcgtaa | gtcggctgac | ccggcaaacc | ctggccctca | tcctggcggg | 960 |
| cgggcgcgga | agtcggctgc | agaagctcac | ggaatggcgc | gccaagcctg | ctgtcccgtt | 1020 |
| cggcggcaaa | ttccggatca | tcgacttccc | gctgtccaac | tgcgtcaatt | ccggaatccg | 1080 |
| ccaggtcggc | gtgctgaccc | agtacaaggc | ggactcactg | atccgccaca | ttcagcaggg | 1140 |
| ctggggcttc | ctgcgcggag | agctcggcga | gttcatcgac | atcatgcctg | cccagcagcg | 1200 |
| tctgcaggaa | agctggtacg | caggcacggc | ggatgcggtg | tatcagaact | ggacatcat | 1260 |
| ccgccagcgg | gaccccgagt | tcatcatgat | cctggccggt | gaccacgtgt | acaagatgga | 1320 |
| ctacggcctg | atgctggcct | atcacgtgga | aaggaaggcc | gatctcacca | tcggctgcat | 1380 |
| ggaagtgccg | cttgccgatg | cgaaggcatt | cggtgtcatg | cagatggacg | gcgagcagcg | 1440 |
| tatccgaaaa | ttcgtcgaga | agccctccga | tccgccgccc | atgccgaacc | gccccgatca | 1500 |
| cgccgccgca | tccatgggga | tctacatatt | caacacggct | ttcctgttcg | agcagctcat | 1560 |
| caaggatgcc | gacaccccg | gctcgaacca | cgatttcggc | atggacatca | tcccccaggt | 1620 |
| cattcagaaa | taccgcgtct | tcgcctatcg | cttccgcaac | gcccagagcg | gcgtgcaggc | 1680 |
| ctactggcgc | gatgtaggca | cggtggactc | atactgggcc | gccaacatgg | agctgatcgg | 1740 |
| ggtcgatccg | gaactgaatt | tgtacgacca | ggaatggccg | atctggacct | atcaggctca | 1800 |
| gaccccgccg | gccaagtttg | tgttcgacga | tgacgaccgg | cgcggcatgg | cggtggactc | 1860 |
| catggtttcg | ggcggctgca | tcatttccgg | cgccgaagtc | cgccactcgt | tgctgttttc | 1920 |
| gaatgtacgg | gtgaactcgt | tttcacgcgt | gctggattcg | gtgatcctcc | ccgacgtgaa | 1980 |
| catcgggcgc | cattgcagga | tcagccgggc | ggtgatcgac | aagggttgca | atattccgcc | 2040 |
| caataccgtc | atcggcgaaa | acctcgagga | tgaccgcaaa | cggttttacg | tcagccccga | 2100 |
| gggcatcgtt | ctggtgaccc | ccgattgtct | cggccagagg | ctgcatttcc | accgctgatt | 2160 |

```
gcgattcgga aggtgcaggc cggagggtcc ggaccgccgc tccacccgtt gttttcggtg    2220
tcacagcccc atggatgctc acggaatttt cgaccggcgc cgcgcgggta ttctgctcca    2280
catcagttcc ctgcccggcg gaccgggaaa cggcgatctg ggggccgaat ccttccgttt    2340
cgtggatttc ctcgctgcgg cgggtgtttc ggtatggcag acactgccca tcaatcccac    2400
ccacgaggac ggttcacctt atcagtgtac atccgtgcac gccggcaatc cgctcttgat    2460
cgggttggac tggttgattg c                                              2481

<210> SEQ ID NO 9
<211> LENGTH: 189
<212> TYPE: DNA
<213> ORGANISM: Artificial Sequence
<220> FEATURE:
<223> OTHER INFORMATION: in-frame deletion of glgA2

<400> SEQUENCE: 9
atgccggaaa gccgggccga ggttgcgccg gagccgtcgc cccgcctca catccagcac      60 cggcccgccc tgttcgtggt ccatgtcacg ttccgcgagc tgatgaagaa tgccatgcgc     120
tacgactatt cctggaacca tccggggcag gactatctca acatttacca ctatatccgg     180
gacaaatag                                                             189

<210> SEQ ID NO 10
<211> LENGTH: 2499
<212> TYPE: DNA
<213> ORGANISM: Methylococcus capsulatus

<400> SEQUENCE: 10
atggcaagca agaaatctga tccgaaaaag accgcgccgg ccccggatgc accggaacac       60
acccgcaccg gcatgagccc ggaaattctc aaggccgcct tcatcgacaa cctcacactg      120
gccgtgggtc gccccctgga aacggcggtg cccgaggact ggtaccaagc catcgcactg      180
tcggtgcgcg accgcatcat gcagcgctgg gtccgccagt tcgaaaaacg caatgccccc      240
gacgtacgcc aggtcgccta cctgtcggcg gaattcctcc ccggtccgca tctgggcaac      300
agcctgctca atctcggcat caccgacaat gcccgcgagg cactgccgg ccaggacctc      360 gacctgtaca ttggactgga ggaggaaccg ggcctcggca acggcggcct ggggcggctc      420
gcggcctgct atctgggactc cctggcgacg ctgcgatacc cggcgacggg ctatggcatc      480
cgctacgaat cggcatcttt cgaccaagcc atcaaggacg gatggcaggt ggagaccacc      540
gacaaatggc tgctgcccgg caacgtctgg gaaatcaagc ggccgaactt cgcccaggtg      600
gtcaagatcg gcggacatac cgagactttt accgaccagc acggcgcctt ccgggtgcgc      660
tggataccgg accgcgtggt ggtcggcgta ccctacgaca cacccatcgt cggctatttg      720
tccgactcct gcgtcctgct ccggctgtgg agtgcggagg cggcccagtc gttcgacttc      780
gccgacttca accggggcga ctattacggc gcggtgagg agaaagtctt ttccgagaac      840
atctcgaaag tcctttaccc caacgatgag cagctcgagg gcaagcgcct gcgcctggaa      900
cagcagtatt tcttcgtcgc ctgctcgatc aaggacatga tccgcctgtg cttgcggcgg      960
ggctcgacgc tggagcgctt ccacgagatg ttctgtgtcc agctcaacga cacccacccg     1020
gccatcgccg tggcggagct gatgcggcaa ttggtggaca aatatgccat gccgtgggag     1080
cgggcctggg acatcacccg ccggaccttc tcctacacca atcacacgct gttgccgag      1140 gccctggaaa aatggccgct gccgctgttc ggctcggtgc tgcccggca cctggaaatc     1200
```

| | |
|---|---:|
| gtctacgaga tcaaccgccg cttcctcgac gaggtccgca cccgtttccc aggggacgag | 1260 |
| gacaagatcg cgcggctgtc gatcatcgac gagagcggcg agaaatacgt gcgcatggcc | 1320 |
| aacctggcga tggtcgggag ccacaccgtc aacggcgtcg cggaattgca ctccgagctg | 1380 |
| gtgaagaccc agctcttccc ggacttccac gacctcgacc cgaagcgttt ccagaacgtg | 1440 |
| accaacggcg tcacgccgcg cgcttcctg gggctgagca tccgggact gaccaggctg | 1500 |
| atcgacgggt gcatcggcga cagctggctg tcggatctgg accggctcag ggagctggag | 1560 |
| gctttcgccg gcgatgccgg gttccagcag gactggatgc ggatcaagct ggaaaacaag | 1620 |
| agccggctgg ccaggatcat ccgcgaccgc accggtgtcg tggtcgaccc gacctcgctg | 1680 |
| ttcgacatcc aggtcaagcg catccacgaa tacaaacgcc agcacctgaa cgtgctgcac | 1740 |
| atcatcacgc tgtaccagcg cctcaagcac gatcccagac tgcagatcac gccccggacc | 1800 |
| ttcctgttcg gcggcaaggc cgcacccggc tattacatgg ccaagctgat catcaagctg | 1860 |
| atcaacgccg tcgcagacac cgtgaatcag gaccccgcgg tgcgcgatct catcaaggtc | 1920 |
| gtattcctgc cggactacaa cgtcaagcac gcgcagaaca tctacccggc ggccgacctg | 1980 |
| tccgagcaga tctccaccgc cggcaaggag gcctcgggca ccggcaacat gaaactgtcg | 2040 |
| ttgaacggcc gcctgaccat cggcacgctg gacggcgcca acgtcgaaat ccgtgaagag | 2100 |
| gtgggggcgg agaatttctt cctgttcggc ctgacctgcg agcaggcagc ccggctcagg | 2160 |
| gccgacggct acaatcccgg cgactactgc acggtgatcc ggaactgcg gggcgtcatc | 2220 |
| gaactgatcg acagcggcct gttctcccac ggcgacaggg agctgttccg accgctcacc | 2280 |
| gcgcacctgc tggaacggga cgattatctg ctgatggccg actatcggcc ctacgtcaac | 2340 |
| tgccagcagc aggtggggca cgcctaccgt gactgtcagc actggacccg catgtccatc | 2400 |
| ctcaacgtcg cccgcatggg caagttttcg tcggaccggg cggtacggga gtacgcggcg | 2460 |
| aacatctgga aactgaaacc cttcaccccc gacccatga | 2499 |

<210> SEQ ID NO 11
<211> LENGTH: 2511
<212> TYPE: DNA
<213> ORGANISM: Methylococcus capsulatus

<400> SEQUENCE: 11

| | |
|---|---:|
| atgctcacgc gcaagttcaa gaccagcaac ccgaccgcgc tcctgacaga atgccgggt | 60 |
| ctgggaatgg gggccaaaaa cctcagcgcc gacatccgcc ggcatttcaa ctgcactctg | 120 |
| gggcgggacc gtgactgccg ctcggtacac tatgcctact cggcgctggc gttgacggtg | 180 |
| cgtgaccgcc tcatggagcg ctggcggaac accgaatatg cctacgatca ggcggattgc | 240 |
| cgccggactt attacctctc gctggagttc ctgctcggcc gcgccctgag caacgcgatg | 300 |
| ctgaacctcg ggatcgagga gcccatccag caggcgctca tgaactgggt ctggaactgg | 360 |
| gaagagttgg cggattcgga gttcgatgcc ggcctcggca tggcgggct ggggcggctc | 420 |
| gcggcctgct tcatcgacag ttgcgccacg ctgcagcttc cggtgatggg gtacggcatc | 480 |
| cgttacgaat acggcatgtt ccgccagatg atcgtcaatg gttaccaggt cgaggagccc | 540 |
| gaccactggt tgcggaatgg tcacgtatgg gagcaggagc gccggagct gacggtgcgg | 600 |
| gtcaagttcg gcggccggac cgagttctcc aacgatgtgt cgcggccggg tcaggtggta | 660 |
| tggctcgaca ccgatgacgt gctggccgta cccttcgaca tcccggtgcc gggataccgg | 720 |
| aacggcacgg tcaacaccct gaggctatgg aaatccgctg ccactgacga attcaagctg | 780 |
| ggcgagttca tgccggtga ctatgccgaa tccgtccgcg ccaagaatct ggcggaaaac | 840 |

```
atctcgatgg tgctgtatcc gaacgatgcc agcgagaacg gcaaggaact tcggctgcgc      900
cagcagtatt tcctggcgtc ggccagcctg caggacgtgc tgcggcggtg gctggcggac      960
cacggcgagg atttctcgga gtttgccgag aagaactgct tccagctcaa cgacacccac     1020
ccgaccattg cggtggccga gctgatgcgc ctcttgatcg acgtgcatgg cctggcctgg     1080
aacgaggcct gggccatcac caaccgcacc atggcctaca ccaaccatac cctgttgccc     1140
gaggcgctgg aaaaatggcc ggtgcggctg ttccggcaga tgctgccgcg cctgctggag     1200
atcatcttcg agatcaacgc gcgtttcctg ggcgaggtcg cggcgcgctg gcccggtgac     1260
atcgaccggc tggcacggat gtcgctgatc gaagagggac atgaacaaca ggtgcggatg     1320
gcctatctcg ccatcgtcgg cagcttctcg gtcaatggcg tcgcggccct gcactccgac     1380
ctgctcaagc atggcctgtt caaggacttc cacgaactgt ggccggagcg tttcaacaac     1440
aagaccaacg gcatcacccc ccggcgctgg ctggccgcct gcaatccgga gctggccggc     1500
ctcatcagcg aggccatcgg cgacaagtgg accgccgatc tgacccgtct ggccgaactc     1560
aggccgttcg ccgaggatgc ggcgttccgg gaacggtgga tggcgatcaa gcggcgcaac     1620
aaggagaagc tgctggactt caagaaccgc gagctggggt tgactctggt gaaccccgac     1680
ctgatgttcg acgtccaggt caagcgtatc catgaataca agcgccagtt gctcaacgtg     1740
ctgcacgtga tccatctgtt cgaccggatc aagcggggcg atgtccagga ctggacgccc     1800
cgctgcgtcc tgtttggcgg caaggctgcg ccgggctacg tgatggcgaa gcgcatcatc     1860
aagctcatca caacgtggc aggaacgatc aacggcgatc ccgaaatgaa cgatcgcctg     1920
agtgtgttgt tcctgccgaa ttaccgggtc accgccatgg aggtgatctg tccgggcacc     1980
gatctgtcgg agcagatttc cacggccggc aaggaggcct cgggtaccgg caacatgaag     2040
ttcatgatga acggagcctt gaccatcggc acgctggacg gcgccaacat cgagattcgg     2100
gaggaagtgg gagcggaaaa cttcttcttg ttcggcctga ctgccgagga ggtcgaacgc     2160
cgccgcggtg gctacgatcc cggcgcggtc atcgaggcga acgaggactt gaaacgggtc     2220
atgggactcc tcgagagtgg ttttttcaac cgattcgagc cggcatatt cgatcccatc     2280 atcgaatcga tccgcagtcc tcacgaccct tggatgacgg ctgccgattt ccccggctat     2340
gtcgaggcgc agagagcggc cgcggccgct ttccgcgaca aggatcgctg ggcccggatg     2400
agcatcctga caccgccgc cagcggcaag ttctccaccg accgcaccat cgccgaatac     2460
aatcgcgaga tctggaagct gacgccgata ccggctttgc cggtgaagta a             2511
```

<210> SEQ ID NO 12
<211> LENGTH: 2175
<212> TYPE: DNA
<213> ORGANISM: Methylococcus capsulatus

<400> SEQUENCE: 12

```
atgcggaagg ttgatgatac acttccagct cgccgcgtat tccttggtgt tttgagaatc       60
ggtccgggtc gaggtccggc tgcgatgacg gtgccagcaa aattcgatta tcaacgggga      120
tcgcccttgc ccttgggtgt tcatttccag gggacggatg ccaatttcgc cctgttcagc      180
cggcatggtt cccgggtccg cctgttattg tttgccgacc ccagccacac ccggcctcac      240
caagtcatcg atctcgatcc ccatcaccac cgtaccggtg atatctggca cgtggcggta      300
cacggcgcac accgcgggct ggcttacgcc tttcaggtcg acgggccgca tgagccgcat      360
ctgggacatc gtttcgatcc ccaggcggta ctgctcgacc cctatgccac ggctctggtg      420
```

```
acaccggagc attgggagtt ttcgggggct gcggtcggcg ggccggaggg agtggtcgca    480
aaggcgctgg tcacggcaga ccatttcgac tgggggcatg accgtccgct caagcatcac    540
tggtcggagc tggtcatcta tgaggcccat gtgcgggggc tgagcattca tccttcgtcg    600
gcagtgcgga tcccggcac ctacctcggc gtcatcgaca agattcccta cttcaaacgg    660
ctcggaatca ccgccctcga actgatgccg ctgcaggcgt tcaatcctta cgaagtgacc    720
cgctacaacc ccgtcaccgg cgagcggctc cggaactact ggggctacaa caccatcgcc    780
ttccaggcgc cgcatgccgg ttatggaacc ggcgcctacc ccggctgcca ggtggaagag    840
ttcaagcgca tggtcaaggc tctgcacgag gccgacatcg aggttctcct cgatgtcgtg    900
ttcaaccaca ccgcggaagg cgatgagacc ggccccatcc tgaacttccg cggtctggac    960
aacagcattt actacctgct ggaagaagac cgccggcatt accgcaacta ttcgggctgc   1020
ggtaacaccg tcaactgcaa tcacccggta gtgcgcagct acattctgga ctgcctgcgg   1080
tactgggtgg tcgagatgca cgtggatggg ttccggttcg atctggcctc gatcctgggg   1140
cgcgaccgca acggccatct ggtgcccaat ccaccgctgc tggagctgat cgccgaggat   1200
cccatcctgc gcgacgtcaa gctcatcgcc gaggcctggg atgccggcgg cgcctatctg   1260
gtcgggcgtt tcccgggcga gcgctggtgc gaatggaacg gcgtgtaccg ggacgacgtg   1320
cgccgctact ggcgcggcga tccgggtatg gcggggcct ttgccagccg cctgtgcggt    1380
agtgccgaca tttacgagca ttccggcaag gcgcctgtga acagcatcaa cttcgtgact   1440
tgccacgacg gcttcacgct caacgatctg gtcagctatg catgcaaaca caattccgcc   1500
aacggggagg acaaccgcga cggttcggac cacaacttca gcgccaatta tggctgtgag   1560
gggccgaccg gcgatcacgg gatcaacgcc gtccgccgcc gccagatgaa gaacttgatg   1620
gcctcgctgc tgctgtcaag gggagtgccc atgatcctgg gcggcgacga gttctgccgg   1680
acccagcggg ggaacaataa cgcctactgt caggacaacg agatctcctg gttcgactgg   1740
cgtttgctgg acgagaaccg ctcgttcttc gagttcgtcc gcaagatgat cgcattccgg   1800
gcccgccatc cggtgctgtc gcgggagcag ttctaccggc cggaagatat tctctggttc   1860
agcccggccg gtggccagcc ggactggcag gcggacgctg cgctgggttg ctgcattcgg   1920
gcggtggggg gcgaggagca accgctgtgt ctgctgttca atccgacggc ggagggctc   1980 tgcttccggc tgccggatac gcttcgcggc ggggtgtgga tcaaggccgt cgataccgcc   2040
gtggaatcgc cttgtgacat ctgcgaactc gaagggggga gtccgctgcc ggatcagcgg   2100
cggctgttcc tccccgaccg cagcctggtg gtgctggtgg aagggccgc gacggctgcc   2160 gcggcccgtg cctga                                                    2175

<210> SEQ ID NO 13
<211> LENGTH: 603
<212> TYPE: DNA
<213> ORGANISM: Methylococcus capsulatus

<400> SEQUENCE: 13
atgacccggg agttcgaggt tctgcgggag gagcggcttc acggcggatt cttcacgctg     60
ctgcggctgc ggctgcgcca caccctccac ggcggcggct ggagcgaaat cgtcacgcgc    120
gagctgtacc acaggagcag ttgcgtggcg gtcattcctt acgatccggt ggccgaccgg    180
gtggtgctga tcgaacagtt ccgggtcgga ccgctcaaat cggggggaaaa tccctggttg   240 ctggaaatcg tcgccggtgc tgtggaaccg ggcgaacata cggacgaagt ggcccatcgc    300
gagacgttgg aagaggccgg agcccagatt cgtgaactca tccccgtgtc ggagttcttc    360
```

```
accacaccgg gtggctgctc ggaaagcatc actctttact gcggcatcgt ggattcttcc    420
tgcctcggcg gaatccacgg tctggccgag gagcacgaag acatcctggt cagcgtggtc    480
gattttgccg cggcgatgac cctgctcgcc gaagggcgga ttcggtcggc catcccgatc    540
atcggcctgc agtggctggc gctgaaccgg gagcgtctca ggatgcagta cggggtggcc    600
tga                                                                  603
```